United States Patent
Kane et al.

(10) Patent No.: US 10,117,883 B2
(45) Date of Patent: *Nov. 6, 2018

(54) METHODS AND COMPOSITIONS FOR TREATING SYMPTOMS OF DISEASES RELATED TO IMBALANCE OF ESSENTIAL FATTY ACIDS

(71) Applicant: BODYBIO INC., Millville, NJ (US)

(72) Inventors: Edward Kane, Millville, NJ (US); Patricia Kane, Millville, NJ (US); Brett T. Hauser, Millville, NJ (US)

(73) Assignee: BODYBIO INC., Millville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/646,342

(22) Filed: Jul. 11, 2017

(65) Prior Publication Data

US 2017/0319607 A1    Nov. 9, 2017

Related U.S. Application Data

(60) Provisional application No. 61/969,070, filed on Mar. 21, 2014.

(51) Int. Cl.

| | | |
|---|---|---|
| A61K 31/685 | (2006.01) | |
| A61K 31/05 | (2006.01) | |
| A61K 31/202 | (2006.01) | |
| A61K 31/352 | (2006.01) | |
| A61K 31/353 | (2006.01) | |
| A61K 31/454 | (2006.01) | |
| A61K 31/661 | (2006.01) | |
| A61K 31/683 | (2006.01) | |
| A61K 36/185 | (2006.01) | |
| A61K 36/285 | (2006.01) | |
| A61K 45/06 | (2006.01) | |
| A61K 31/6615 | (2006.01) | |
| A61K 9/127 | (2006.01) | |

(52) U.S. Cl.
CPC .......... *A61K 31/685* (2013.01); *A61K 9/1277* (2013.01); *A61K 31/05* (2013.01); *A61K 31/202* (2013.01); *A61K 31/352* (2013.01); *A61K 31/353* (2013.01); *A61K 31/454* (2013.01); *A61K 31/661* (2013.01); *A61K 31/6615* (2013.01); *A61K 31/683* (2013.01); *A61K 36/185* (2013.01); *A61K 36/285* (2013.01); *A61K 45/06* (2013.01)

(58) Field of Classification Search
CPC .... A61K 31/685; A61K 9/1277; A61K 31/05; A61K 31/352; A61K 31/353; A61K 31/454; A61K 31/661; A61K 31/6615; A61K 31/683; A61K 36/185; A61K 36/285; A61K 45/06
USPC .......................................................... 514/78
See application file for complete search history.

(56) References Cited

U.S. PATENT DOCUMENTS

| | | | | |
|---|---|---|---|---|
| 9,655,910 B2 * | 5/2017 | Kane | .................... | A61K 31/685 |
| 2015/0265636 A1 * | 9/2015 | Kane | .................... | A61K 31/685 514/78 |

* cited by examiner

*Primary Examiner* — Yevgeny Valenrod
(74) *Attorney, Agent, or Firm* — Law Offices of Khalilian Sira, LLC; Houri Khalilian; Serge Sira

(57) ABSTRACT

This invention relates to compositions containing combinations of a balanced phosphatidylcholine composition and one or more cannabinoids, a natural or synthetic derivative thereof, or a salt thereof, and kits containing such combinations and methods of using such combinations to treat subjects suffering from an imbalance of fatty acids and related diseases or disorders. This invention also relates to the synergistic effect of such combination therapies in humans.

12 Claims, No Drawings

METHODS AND COMPOSITIONS FOR TREATING SYMPTOMS OF DISEASES RELATED TO IMBALANCE OF ESSENTIAL FATTY ACIDS

CROSS REFERENCE TO RELATED APPLICATIONS

This application claims priority to U.S. Provisional Application No. 61/969,070, filed Mar. 21, 2014, U.S. Provisional Application No. 61/969,068, filed Mar. 21, 2014, U.S. Provisional Application No. 61/969,063, filed Mar. 21, 2014, and U.S. Provisional Application No. 61/969,069, filed Mar. 21, 2014, the entire contents of each of which are incorporated herein by reference.

FIELD OF THE INVENTION

Described herein is a cannabinoid-based combination therapy suitable for local and systemic delivery to a subject; compositions for delivering such pharmaceutically active agents and the use of such compositions in treating and preventing diseases and disorders related to imbalance of essential fatty acids.

I. BACKGROUND OF THE INVENTION

There are a wide variety of diseases and disorders that are caused by or result from cell membrane dysfunction and imbalance and derangement of fatty acids. It has been discovered that diseases and disorders such a seizures, Alzheimer's disease, depression, and atherosclerosis are either caused by or result in or from an imbalance of essential fatty acids in cell membranes.

Seizures

Over 53 million people worldwide suffer from epilepsy. Epilepsy primarily affects children and young adults. Epilepsy and seizures affect nearly 3 million Americans of all ages, at an estimated annual cost of $17.6 billion in direct and indirect costs. Approximately 200,000 new cases of seizures and epilepsy occur each year. Ten percent of the American population will experience a seizure in their lifetime. Almost 50% of new epilepsy cases occur prior to age 25. About 28% of epileptic patients have intractable epilepsy that is resistant to antiepileptic treatment [Antiepileptic Drugs; eds. R. H. Levy, R. H. Mattson and B. S. Meldrum; 4th Edition, Raven Press, NY, N.Y.; Aicardi, Epilepsy in children, 2d Edition, Raven Press, 1994].

A seizure is a paroxysmal event due to abnormal, excessive, hypersynchronous discharges from an aggregate of central nervous system (CNS) neurons, while epilepsy is a condition in which a person has recurrent seizures due to a chronic, underlying process. Experimental and clinical data indicate that the occurrence of repeated seizures can lead to an epileptic condition. Abnormal electrical discharges can arise in the brain due to various electrical or chemical stimuli. Certain regions of the brain including the temporal lobe and the deep nuclear aggregates of the motor cortex, the amygdala and the hippocampal structures of the limbic system are particularly sensitive to abnormal electrical discharges. An alteration in membrane permeability to extracellular calcium appears to be a critical event in the genesis of these abnormal electrical discharges and probably precedes paroxysmal neuronal discharge associated with epileptic seizures.

Epilepsy is a collective designation for a group of central nervous system disorders having in common the spontaneous occurrence of seizures associated with the disturbance or loss of consciousness. These seizures are usually, but not always, associated with characteristic body movements (convulsions) and sometimes autonomic hyperactivity. Seizure in epilepsy detonation is believed to originate in the non-specific subcortical mesodiencephalic reticular systems and diffuse bilaterally into the cerebral cortex. The motor cortex, the amygdala and the hippocampus have a low threshold and high susceptibility to seizure possibly due to the vulnerability of their vasculature to compression and biochemical disturbances. See, e.g., Glaser, "The Epilepsies," Textbook of Medicine, Beeson and McDermott, eds., W B Saunders Co., Philadelphia, 1975, pp. 723-24.

Epileptic seizures are divided into partial and generalized seizures on the basis of the clinical manifestations of the attacks and the electroencephalographic (EEG) pattern. Each of these two general epileptic categories is then further subdivided into three or more subcategories depending on the classification scheme employed. The International Classification of Epileptic Seizures divides seizures into i) partial seizures (beginning locally) including simple partial seizures (consciousness not impaired) with motor symptoms, with somatosensory or special sensory symptoms, and with autonomic symptoms, ii) complex partial seizures (with impairment of consciousness) including beginning as simple partial seizures and progressing to impairment of consciousness, with no other features, with features as in simple partial seizures, with automatisms, with impairment of consciousness at onset, with no other features, with features as in simple partial seizures, and with automatisms, iii) partial seizures secondarily generalized, iv) generalized seizures (bilaterally symmetrical, without local onset) including absence seizures, atypical absence seizures, myoclonic seizures, clonic seizures, tonic seizures, tonic-clonic seizures, and atonic seizures) and v) unclassified epileptic seizures (data inadequate or incomplete).

Accurate diagnosis of epilepsy and seizures is essential since pharmacotherapy is highly selective for a particular type of epileptic seizure. For the treatment of epilepsy, drugs for oral administration such as Phenytoin, Carbamazepine, Valproic acid, Phenobarbital, ethosuximide, Clonazepam, clobazam and Primidone have been used. Recently, the treatment of epilepsy becomes more advanced owing to the newly developed drugs like vigabatrin, Zonisamide, Lamotrigine, topiramate, Oxcarbazepine and Gabapentine, etc. However, the results of the treatment of epilepsy using the said medicines are not satisfactory. The chances of controlling epilepsy with a single medicine are 60-70% and 20-25% requires co-administration of different medicines. The last 10% does not show any improvement with any of the said medicines.

It would therefore be extremely beneficial if there were a way to provide a combination therapy that simultaneously provides amelioration or treatment of epilepsy or related seizure diseases or disorders while at the same time addressing health issues associated with depleted phosphatidylcholine levels and increased sphingomyelin levels in cell membranes. Accordingly, there is a long felt need for discovering new compositions and methods that can achieve such therapeutic effects in patients with epilepsy or related seizure diseases or disorders.

The present invention as disclosed and described herein provides methods and compositions for a combination therapy that can be used to treat or ameliorate epilepsy or related seizure diseases or disorders indications while simultaneously addressing or clarifying or reducing higher sphingomyelin to phosphatidylcholine ratios.

Alzheimers

Alzheimer's disease ("AD") is a dementing disorder characterized by progressive impairments in memory and cognition. It typically occurs in later life, and is associated with a multiplicity of structural, chemical and functional abnormalities involving brain regions concerned with cognition and memory. This form of dementia was first reported by Alois Alzheimer in 1907 when he described a disease of the cerebral cortex in a 51-year-old woman suffering from an inexorably progressive dementing disorder. Although other forms of dementia had been well characterized at the time of Alzheimer's clinical report, his patient was clinically and pathologically unusual, because of her relatively young age and the presence of the then newly described intra-cellular inclusions which have subsequently come to be known as neurofibrillary tangles (NFTs). In recognition of this unique combination of clinical and pathological features, the term "Alzheimer's Disease (AD)" subsequently came into common usage.

Alzheimer's disease is the most common form of dementia. As of December 2013, this number is reported to be 36 million-plus worldwide. The prevalence of Alzheimer's is thought to reach approximately 107 million people by 2050. The cause and progression of Alzheimer's disease are not well understood. The progressive formation of amyloid plaques and vascular deposits of amyloid .beta.-peptide has long been considered the pathological hallmark of Alzheimer's disease. Only a few medications have currently been approved by FDA for treating the cognitive manifestations of AD, but none has indication of delaying or halting the progression of the disease.

In Alzheimer's disease (AD), the abnormal cleavage of beta amyloid protein precursor from the intracellular membrane often produces a protein $A_\beta 1$-42 which is incompletely removed by normal clearance processes. It has been reported that soluble β amyloid oligomers are highly neurotoxic. Moreover, over time, this soluble protein assemblage is deposited as a β amyloid protein $A_\beta$ plaque within brain tissue, leading to the local destruction of neurons. The $A_\beta$ plaque deposition is also believed to provoke an inflammatory response by microglia and macrophages, which recognize the plaque as a foreign body. These cells are believed to respond to the plaque deposition by releasing pro-inflammatory cytokines and reactive oxygen species (ROS). Although the inflammatory response may be provoked in an effort to clear the brain tissue of the detrimental plaque, it is now believed that this inflammation also injures local neuronal tissue, thereby exacerbating AD. Soluble oligomers of β amyloid or "ADDLs" are a neurotoxic species implicated in AD pathogenesis. Yang, J. Biol. Chem., 280, 7, Feb. 18, 2005, 5892-5901.

Alzheimer's disease (AD) is characterized by the extracellular accumulation of amyloid plaques in the brain composed of the 40 or 42 amino acid $A_\beta$ peptide. This extracellular accumulation of the $A_\beta$ 42 peptide is the hallmark pathology of the disease state and therefore thought to be the most important player in the cause of Alzheimer's disease. While another common lesion of the Alzheimer's disease brain is the presence of intracellular neurofibrillary tangles made up of abnormally phosphorylated tau, a microtubule-associated protein, currently, most evidence suggests that $A_\beta$ plays the central role in the pathogenesis of the disease. Nevertheless, the etiology of Alzheimer's disease is still poorly understood.

Recent advances in molecular genetics has suggested several genetic links to Alzheimer's disease including mutations in the amyloid precursor protein (APP), the presenilin 1 protein, .alpha.-2 macroglobulin (A2M), nicastrin, and APOE.epsilon.4. The chromosomal "hotspot" for late onset Alzheimer's disease (>65 years of onset, LOAD) has been mapped to 10 q. In contrast, the genetic loci for familial early onset Alzheimer's disease (<65 years of onset, EOAD) maps specifically to APP mutations at the .gamma.-secretase site or mutations in the presenilin 1 gene known to affect y-secretase activity. It is important to distinguish the difference between the genes linked to LOAD and EOAD. Most, if not all of the EOAD mutations found in presenilin, nicastrin, or the APP y-cleavage site, are linked to y-secretase cleavage. On the other hand, the genes linked to LOAD have no common link to Alzheimer's except for their ability to alter $A_\beta$ secretion from cells or clearance in the brain. Therefore, it seems clear that EOAD is caused by a specific defect in the y-secretase activity, while the specific defect(s) in LOAD is still not clear.

The $A_\beta$ peptide is generated by the endoproteolytic cleavage of the amyloid precursor protein (APP), a large type I transmembrane protein. The two enzymes that cleave APP in the amylogenic pathway are called the β- and .gamma.-secretases which cleave APP from the N- and C-termini, respectively. In this pathway, the β-secretase (BACE) is the rate limiting enzyme in the cleavage of APP, producing a sAPP-.beta. fragment that is secreted from the cell and a C99 fragment that is left in the membrane. The C99 fragment is the substrate for the .gamma.-secretase (GACE) which cleaves C99 to produce A β and a C99 "stub" that seems to function in a complex with Tip60 and Fe65 which derepresses a gene in the NF.kappa.-B pathway through IL-1.beta., KAI1 (a tetraspanin cell surface molecule). The genetic, biochemical, and molecular evidence for Alzheimer's suggests LOAD is likely to be polygenic and involve one or more genetic defects, familial and/or spontaneous.

In spite of the many research investigations and diverse studies undertaken to date, present clinical evaluations still cannot establish an unequivocal diagnosis of Alzheimer's disease. To the contrary, the only presently known means for positively proving and demonstrating Alzheimer's disease in a patient can only be achieved by a brain biopsy or a postmortem examination to assess and determine the presence of NFTs and senile (amyloid) plaques in brain tissue. Instead, a set of psychological criteria for the diagnosis of probable Alzheimer's disease has been described, and includes the presence of a dementia syndrome with defects in two or more areas of cognition, and progressive worsening of memory and other cognitive function over time. However, by the time these psychological changes may be observed, significant irreversible neuronal damage has already occurred.

Furthermore, only a limited number of pharmacological agents heretofore have been identified as effective in treating symptoms of Alzheimer's disease in a person suffering therefrom. The most prominent of these today are tacrine and donepezil hydrochloride, which are cholinesterase inhibitors active in the brain. These drugs do not slow the progress of the disease. Furthermore no compound has been established as effective in blocking the development or progression of Alzheimer's disease although a number of compounds, including estrogen, ibuprofen, selegiline, are thought to possibly have this capability and are being investigated for therapeutic use for this purpose.

It is therefore clear that there has been and remains today a long standing need for compositions and methods to treat Alzheimer's disease in a living human subject before the disease has manifested far enough to produce psychological changes, thereby allowing earlier and more effective therapeutic intervention. It would therefore be extremely beneficial if there were a way to provide a combination therapy that simultaneously provides amelioration or treatment of Alzheimer's disease or related diseases or disorder while at the same time simultaneously addressing other health issues related to depletion of phosphatidylcholine levels and increased sphingomyelin levels in cell membranes. Accordingly, there is a long felt need for discovering new compositions and methods that can achieve such therapeutic effects in patients with Alzheimer's disease or related disorders or diseases.

The present invention as disclosed and described herein provides methods and compositions for a combination therapy that can be used to treat or ameliorate Alzheimer's disease or related diseases or disorder while simultaneously addressing or clarifying or reducing higher sphingomyelin to phosphatidylcholine ratios.

Atherosclerosis

Over 50 million Americans have cardiovascular problems, and many other countries face high and increasing rates of cardiovascular disease. It is the number one cause of death and disability in the United States and most European countries. By the time that heart problems are detected, the underlying cause, atherosclerosis, is usually quite advanced, having progressed for decades.

Atherosclerosis is a polygenic complex disease of mammals characterized by the deposits or plaques of lipids and other blood derivatives in the arterial walls (aorta, coronary arteries, carotid arteries). These plaques can be calcified to a greater or lesser extent according to the progression of the process. They are also associated with the accumulation of fatty deposits consisting mainly of cholesterol esters in the arteries. Cholesterol accumulates in the foam cells of the arterial wall, thereby narrowing the lumen and decreasing the flow of blood. This is accompanied by a thickening of the arterial wall, with hypertrophy of the smooth muscle, the appearance of foam cells and the accumulation of the fibrous tissue. Hypercholesterolemia can therefore result in very serious cardiovascular pathologies such as infarction, peripheral vascular disease, stroke, sudden death, cardiac decompensation, cerebral vascular accidents and the like.

The cholesterol is carried in the blood by various lipoproteins including the low-density lipoproteins (LDL) and the high-density lipoproteins (HDL). The LDL is synthesized in the liver and makes it possible to supply the peripheral tissues with cholesterol. In contrast, the HDL captures cholesterol molecules from the peripheral tissues and transports them to the liver where they are converted to bile acids and excreted. The development of atherosclerosis and the risk of coronary heart disease (CHD) inversely correlate to the levels of HDL in the serum. Gordon et al. (1989) N. Engl. J. Med. 1989 Nov. 9: 321: 1311; Goldbourt et al. (1997) Thromb Vasc. Biol. 17: 107. Low HDL cholesterols often occur in the context of central obesity, diabetes and other features of the metabolic syndrome. Goldbourt et al., supra. It has been suggested that low HDL cholesterol levels are associated with an increased risk of CHD, while high concentrations of HDL have a protective effect against the development of premature atherosclerosis. Gordon et al. (1986) Circulation 74: 1217. Studies demonstrated that the risk for developing clinical atherosclerosis in men drops 3% with a 1% increase in the concentration of HDL in plasma. Gordon et al. (1989) N. Engl. J. Med. 321: 1311. It has been established that concentrations of LDL cholesterol can be reduced by treatment with statins, inhibitors of the cholesterols biosynthesis enzyme 3-hydroxyl-3-methylglutaryl Coenzyme A reductase and thereby this treatment has been used as a successful approach for reducing the risk for atherosclerosis where the primary indication is high LDL level. However, it remains unclear whether statins are beneficial for patients whose primary lipid abnormality is low HDL cholesterol.

Angina pectoris is a severe constricting pain in the chest, often radiating from the precordium to the left shoulder and down the left arm. Often angina pectoris is due to ischemia of the heart and is usually caused by coronary disease.

Currently the treatment of symptomatic angina pectoris varies significantly from country to country. In the U.S., patients who present with symptomatic, stable angina pectoris are frequently treated with surgical procedures or PTCA. Patients who undergo PTCA or other surgical procedures designed to treat angina pectoris frequently experience complications such as restenosis. This restenosis may be manifested either as a short term proliferative response to angioplasty-induced trauma or as long term progression of the atherosclerotic process in both graft vessels and angioplastied segments.

The symptomatic management of angina pectoris involves the use of a number of drugs, frequently as a combination of two or more of the following classes: beta blockers, nitrates and calcium channel blockers. Most, if not all, of these patients require therapy with a lipid lowering agent as well. The National Cholesterol Education Hypertension frequently coexists with hyperlipidemia and both are considered to be major risk factors for developing cardiac disease ultimately resulting in adverse cardiac events. This clustering of risk factors is potentially due to a common mechanism. Further, patient compliance with the management of hypertension is generally better than patient compliance with hyperlipidemia. It would therefore be advantageous for patients to have a single therapy which treats both of these conditions.

Coronary heart disease is a multifactorial disease in which the incidence and severity are affected by the lipid profile, the presence of diabetes and the sex of the subject. Incidence is also affected by smoking and left ventricular hypertrophy which is secondary to hypertension. To meaningfully reduce the risk of coronary heart disease, it is important to manage the entire risk spectrum. For example, hypertension intervention trials have failed to demonstrate full normalization in cardiovascular mortality due to coronary heart disease. Treatment with cholesterol synthesis inhibitors in patients with and without coronary artery disease reduces the risk of cardiovascular morbidity and mortality.

Currently there is no cure for atherosclerosis. Pharmaceuticals such as Statins, Fibrates, and Hypertension medications are helpful in lowering bad cholesterol (LDL), slight reductions in arterial plaque, and improvements in vasodilatation; all of which are symptomatic of Atherosclerosis. Unfortunately, for some of the millions of individuals at risk or dealing with this disease, lifestyle changes (i.e. diet and exercise) and combinations of these drugs are simply not enough.

It would therefore be extremely beneficial if there were a way to provide a combination therapy that simultaneously provides amelioration or treatment of atherosclerosis or related coronary heart disease indications while at the same time simultaneously addressing other health issues associated with depleted phosphatidylcholine levels and increased sphingomyelin levels in cell membranes. Accordingly, there is a long felt need for discovering new compositions and methods that can achieve such therapeutic effects in patients with atherosclerosis or related coronary heart diseases.

The present invention as disclosed and described herein provides methods and compositions for a combination therapy that can be used to treat or ameliorate atherosclerosis or related coronary heart disease indications while simultaneously addressing or clarifying or reducing higher sphingomyelin to phosphatidylcholine ratios.

Depression

Recent estimates indicate that more than 19 million Americans over the age of 18 experience a depressive illness each year. The American Psychiatric Association recognizes several types of clinical depression, including mild depression (dysthymia), major depression, and bipolar disorder (manic-depression). Major depression is defined by a constellation of chronic symptoms that include sleep problems, appetite problems, anhedonia or lack of energy, feelings of worthlessness or hopelessness, difficulty concentrating, and suicidal thoughts. Approximately 9.2 million Americans suffer from major depression, and approximately 15 percent of all people who suffer from major depression take their own lives. Bipolar disorder involves major depressive episodes alternating with high-energy periods of rash behavior, poor judgment, and grand delusions. An estimated one percent of the American population experiences bipolar disorder annually.

Significant advances in the treatment of depression have been made in the past decade. Since the introduction of selective serotonin reuptake inhibitors (SSRIs), i.e., Prozac®, many patients have been effectively treated with anti-depressant medication. New medications to treat depression are introduced almost every year, and research in this area is ongoing. However, an estimated 10 to 30 percent of depressed patients taking an anti-depressant are partially or totally resistant to the treatment. Those who suffer from treatment-resistant depression have almost no alternatives. Thus, there is a need to develop alternative treatments for these patients.

Up to 10% of persons visiting a physician are afflicted with an affective disorder (also known as behavioural disorder, mood disorder). Nonetheless, most cases remain undiagnosed or inadequately treated. Affective disorders include among others, depression, anxiety, and bipolar disorder. These diseases are well described in the literature; see, for example, Diagnostic and Statistical Manual of Mental Disorders—4th Edition Text Revision (DMS-IV-TR), American Psychiatric Press, 2000.

Depression, also known as unipolar affective disorder, is characterized by a combination of symptoms such as lowered mood, loss of energy, loss of interest, feeling of physical illness, poor concentration, altered appetite, altered sleep and a slowing down of physical and mental functions resulting in a relentless feeling of hopelessness, helplessness, guilt, and anxiety. The primary subtypes of this disease are major depression, dysthymia (milder depression), and atypical depression. Other important forms of depression are premenstrual dysphoric disorder and seasonal affective disorder. Present treatment of depression consists of psychotherapy, antidepressant drugs, or a combination of both. Most anti-depressive drugs target the transport of the neurotransmitters serotonin and/or norepinephrine, or the activity of the enzyme monoamine oxidase. They include: Selective serotonin-reuptake inhibitors (e.g., fluoxetine, paroxetine, sertraline, fluvoxamine), tricyclic antidepressants (e.g., amitriptyline, imipramine, desipramine, nortriptyline), monoamine oxidase inhibitors (e.g., phenelzine, isocarboxazid, tranylcypromine), and designer antidepressants such as mirtazapine, reboxetine, nefazodone. However, all existing anti-depressive drugs possess shortcomings such as long latency until response, high degree of non-responders, and undesirable side effects (Holsboer, Biol. Psychol. 57 (2001), 47-65). Therefore, a need exists in the medical community for new anti-depressive drugs with different mechanisms of action and improved pharmacological profile (Baldwin (2001) Hum. Psychopharmacol. Clin. Exp. 16:S93-S99; Greden (2002) J. Clin. Psychiatry 63(Suppl 2): 3-7).

Anxiety disorders are defined by an excessive or inappropriate aroused state characterized by feelings of apprehension, uncertainty, or fear. They are classified according to the severity and duration of their symptoms and specific affective characteristics. Categories include: (1) Generalized anxiety disorder, (2) panic disorder, (3) phobias, (4) obsessive-compulsive disorder, (5) post-traumatic stress disorder, and (6) separation anxiety disorder. The standard treatment for most anxiety disorders is a combination of cognitive-behavioural therapy with antidepressant medication. Additional medications include benzodiazepines such as alprazolam, clonazepam, diazepam, lorazepam, halazepam, chlordiazepoxide, and other drugs such as buspirone, clonidine, pagoclone, risperidone, olanzapine, quetiapine, ziprasidone. Nonetheless, there are a number of unmet needs in the treatment of anxiety disorders including the need for more effective, rapidly acting, and better tolerated medications; effective treatments for refractory disorders; prevention of relapse; and promotion of resilience and long-lasting response (Pollack, Psychopharmacol. Bull. 38(Suppl 1) (2004) 31-37).

Bipolar disorder, also known as manic-depression, is characterized by mood swings between periods of mania (i.e. mood elevation including exaggerated euphoria, irritability) and periods of depression. Bipolar disorder is classified according to the severity of the symptoms. Patients diagnosed with bipolar disorder type I suffer from manic or mixed episodes with or without major depression. In Bipolar Disorder type II, patients have episodes of hypomania and episodes of major depression. With hypomania the symptoms of mania (euphoria or irritability) appear in milder forms and are of shorter duration. The current drugs used to treat bipolar disorders are lithium, valproate and lamotrigine, which stimulate the release of the neurotransmitter glutamate. As with antidepressive drugs, they take weeks to become effective and can result in undesirable side effects, for example, high levels of lithium in the blood can be fatal (Sachs (2003) J. Clin. Psychopharmacol. 23(Suppl. 1):S2-S8).

Cushing's Syndromes are hormonal diseases with an estimated incidence of approximately 10 per 1 million persons (Meier and Biller (1997) Endocrinol Metab Clin North Am 26:741-762). Cushing's Syndromes are associated with an increased blood concentration of cortisol (hypercortisolism) or the presence of glucocorticoid hormone over a long period of time. The most common underlying cause of Cushing's Syndromes are excessive production of ACTH by the pituitary gland. As mentioned above, ACTH stimulates the growth of the adrenal glands and the secretion of other corticosteroids. Elevated ACTH levels are most often produced by pituitary adenomas. Cushing's Syndromes resulting from the production of ACTH in a location other than the pituitary gland is known as ectopic Cushing's Syndromes. Examples of ectopic sites include thymoma, medullary carcinoma of the thyroid, pheochromocytoma, islet cell tumours of the pancreas and oat cell carcinoma of the lung. Symptoms of Cushing's Syndromes include weight gain, central obesity, steroid hypersecretion, elevated urinary cortisol excretion, moon face, weakness, fatigue, backache, headache, impotence, mental status changes, muscle atrophy, and increased thirst and urination. At the pituitary level, CRH stimulates ACTH synthesis. ACTH overproduction by pituitary adenomas leads to excessive glucocorticoid secretion from the adrenal glands which causes endogenous Cushing's Syndromes, characterized by a typical abnormal fat deposition around the neck, thinning of the skin, osteoporosis, insulin resistance, dyslipidemia, myopathy, amenorrhea and hypertension. Fatigue, irritation, anxiety and depression are also common clinical features in these patients (Orth (1995) N. Engl. J. Med. 332:791-803; Dahia and Grossman (1999) Endocr. Rev. 20:136-55).

Although to date no single cause of clinical depression has been identified, it is now generally accepted that there is likely a neurochemical component to it. Typical treatments now often consist of a combination of psychotherapy and medication. Currently, the most commonly used antidepressant medications function generally to regulate brain neurotransmitters such as dopamine, serotonin and norepinephrine. Two classes of compounds, one known as selective serotonin reuptake inhibitors, or SSRIs, and the other known as serotonin and norepinephrine reuptake inhibitors (SNRIs) are widely prescribed for treatment of depression. These antidepressants, such as fluoxetine (Prozac®), sertraline (Zoloft®), venlafaxine (Effexor®) and duloxetine (Cymbalta®) have gained substantial popularity because they cause fewer side effects than earlier antidepressants, such as monoamine oxidase inhibitors (MAOIs). Notwithstanding their improved tolerability, however, SSRIs and SNRIs still cause their share of side effects, including insomnia, nausea and sexual dysfunction. In addition to the associated problems, a major concern with known antidepressants is the time they take to achieve their desired effect. In most cases, it will be a minimum of three to four weeks before a full relief of symptoms is observed. In the case of severe depression, this delay can sometimes be life-threatening. Furthermore, only about two-thirds of patients treated actually respond to modern antidepressants. Thus, there continues to be a need for development of new antidepressant medications that will avoid some or all of the problems observed with those antidepressants currently in use. Based on a novel observation regarding the neurochemical basis for depression, the present invention fills such a need.

It is therefore clear that there has been and remains today a long standing need for compositions and methods to treat depression and its related diseases and disorders in a living human subject before the disease has manifested far enough to produce psychological changes, thereby allowing earlier and more effective therapeutic intervention. It would therefore be extremely beneficial if there were a way to provide a combination therapy that simultaneously provides amelioration or treatment of depression or related diseases or disorder while at the same time simultaneously addressing other health issues associated with depleted phosphatidylcholine levels and increased sphingomyelin levels in cell membranes. Accordingly, there is a long felt need for discovering new compositions and methods that can achieve such therapeutic effects in patients with depression or related disorders or diseases.

The present invention as disclosed and described herein provides methods and compositions for a combination therapy that can be used to treat or ameliorate symptoms of diseases related to seizures, Alzheimers, depression, and atherosclerosis while simultaneously addressing or clarifying or reducing higher sphingomyelin to phosphatidylcholine ratios in the cell membrane.

II. SUMMARY OF THE INVENTION

The present invention is directed to compositions and methods for treating symptoms of disease related to an imbalance of essential fatty acids including seizure, depression, Alzheimer disease, and atherosclerosis, in a subject in need thereof.

In its broadest aspect, a pharmaceutical composition for cannabinoid combination therapy is provided comprising: (a) a therapeutically effective amount of a first composition comprising a balanced PC composition; and (b) a therapeutically effective amount of a second composition comprising one or more cannabinoids, a natural or synthetic derivative thereof, or a salt thereof; wherein said first composition and said second composition are each administered together with a pharmaceutically acceptable carrier or diluent.

In one embodiment of the present invention, the balanced PC composition comprises Phosphotidylcholine (PC), Phosphotidylethanolamine (PE), Phosphatidyl inositol (PI), Phosphatidic Acid (PA), Phosphatidylglycerol (PG), Essential Fatty Acids C18.2 (omega 6) (linoleic acid), C18.3 (omega 3) (alpha linolenic acid) (in an approximate 4:1 ratio), or any combination thereof.

In another embodiment of the present invention, the balanced PC composition comprises phospholipids derived from a variety of plant and animal sources.

In one embodiment, a pharmaceutical composition for combination therapy is provided comprising: (a) a therapeutically effective amount of a first composition comprising a balanced PC composition; and (b) a therapeutically effective amount of a second composition comprising one or more cannabinoids, an isolated natural or synthetic derivative thereof, or salt thereof; wherein said first composition and said second composition are each administered together with a pharmaceutically acceptable carrier or diluent.

In another aspect, a pharmaceutical composition is provided for the prevention, amelioration and/or treatment of symptoms of diseases related to impairment of development and activities of cells and tissues, wherein the pharmaceutical composition comprises at least two compositions, a therapeutically effective amount of a first composition comprising a balanced PC composition and a therapeutically effective amount of a second composition comprising one or more cannabinoids, an isolated natural or synthetic derivative thereof, or salt thereof, in a suitable carrier or diluent.

Thus, in one embodiment, this invention is directed to composition comprising a first composition for use with a second composition for achieving an anti-seizure effect in a subject, wherein said first composition comprises a therapeutically effective amount of a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-seizure effect is manifested by a slowing of the progression of one or more symptoms or effects of seizures including, for example, and not by way of limitation, déjà vu, jamais vu, smell, sound, taste, visual loss or blurring, racing thoughts, stomach feelings, tingling feeling, sudden feelings of fear or anxiousness, nausea, dizziness, numbness, changes in vision, blackout, confusion, uncontrollable muscle spasms, drooling or frothing at the mouth, falling, taste strange taste sensations (aura), clenching teeth, sudden, rapid eye movements, grunting, incontinence, sudden mood changes, deafness/sounds, electric shock feeling, loss of consciousness, spacing out, out of body experience, visual loss or blurring, fear/panic, chewing movements, convulsion, difficulty talking, eyelid fluttering, eyes rolling up, falling down, foot stomping, hand waving, inability to move, lip smacking, making sounds, shaking, staring, stiffening, swallowing, sweating, teeth clenching/grinding, tongue biting, tremors, twitching movements, breathing difficulty, heart racing, after-seizure symptoms (postictal), memory loss, writing difficulty, depression, sadness, fear, frustration, shame/embarrassment, bruising, injuries, sleeping, exhaustion, headache, nausea, pain, thirst, weakness, urge to urinate/defecate, or any combination thereof.

In one embodiment, the therapeutically effective amount of a first composition comprising a balanced PC composition and the therapeutically effective amount of a second composition comprising one or more cannabinoids, an isolated natural or synthetic derivative thereof, or salt thereof compositions are formulated in one or different solutions, are either singularly or both administered in a time-released manner, are either singularly or both administered in a dry formulation, liquid formulation, or are either singularly or both administered parenteraly, orally, transdermally, intranasally, intravenously, or using other routes of administration as described infra.

In one embodiment, the therapeutically effective amount of a first composition comprising a balanced PC composition and the therapeutically effective amount of a second composition comprising one or more cannabinoids, an isolated natural or synthetic derivative thereof, or salt thereof, are administered contemporaneously or are administered at different time intervals.

In another embodiment, the therapeutically effective amount of a first composition comprising a balanced PC composition is administered in any order or is administered both prior to and after the therapeutically effective amount of a second composition comprising one or more cannabinoids, an isolated natural or synthetic derivative thereof, or salt thereof.

In a preferred embodiment, the therapeutically effective amount of a first composition comprising a balanced PC composition and the therapeutically effective amount of a second composition comprising one or more cannabinoids, an isolated natural or synthetic derivative thereof, or salt thereof, are administered to a subject in need thereof in a single dose semi-liquid packet.

In another aspect of the present invention, methods are provided for treating a subject at risk for developing symptoms of diseases related to an imbalance of essential fatty acids and impairment of development and activities of cells and tissues. Such diseases and disorders according to the invention disclosed and claimed herein include seizure, depression, dementia, Alzheimer's disease, and atherosclerosis. In order to delay the onset of the one or more of the underlying symptoms related to the aforementioned diseases, the prevention, treatment and/or amelioration of symptoms need not be complete, so long as at least one symptom of the disease is prevented, treated and/or ameliorated.

In one embodiment, this invention is also directed to a method for treating a subject which has been diagnosed as suffering from seizure or a related disease or disorder and who is in need of therapeutic treatment comprising administering to said subject (a) a therapeutically effective amount of a first composition comprising a balanced PC composition; and (b) a therapeutically effective amount of a second composition comprising one or more cannabinoids, a natural or synthetic derivative thereof, or a salt thereof; wherein said first composition and said second composition are each optionally and independently administered together with a pharmaceutically acceptable carrier or diluent, and wherein said therapeutic treatment is prevention, treatment or amelioration of one or more symptoms of seizure or a related disease or disorder.

In yet another aspect, the present invention is directed to compositions and methods for treating dementia, Alzheimer's disease and related diseases and disorders in a subject in need thereof as disclosed in Applicant's U.S. Provisional Application No. 61/969,068, filed Mar. 21, 2014, entitled Compositions and Methods for Treating Alzheimer's Disease and assigned to BodyBio Inc., the entire contents of which are incorporated herein by reference.

Thus, in one embodiment, this invention is directed to composition comprising a first composition for use with a second composition for achieving an anti-Alzheimer's disease effect in a subject, wherein said first composition comprises a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-Alzheimer's disease effect is manifested by a reduction or amelioration of the progression of signs or symptoms associated with Alzheimers disease including impairment of short term memory, impairment of abstract thinking, impairment of judgment, impairment of language skills, dementia, and mood changes, or any combination thereof.

In another aspect of the present invention, methods are provided for treating a subject at risk for developing symptoms of diseases related to impairment of development and activities of cells and tissues in order to delay the onset of the one or more of the aforementioned underlying symptoms related to Alzheimer's disease. The prevention, treatment and/or amelioration of one or more of the aforementioned symptoms related to Alzheimer's disease need not be complete, so long as at least one symptom of the disease is prevented, treated or ameliorated.

In one embodiment, this invention is also directed to a method for treating a subject which has been diagnosed as suffering from Alzheimer's disease and who is in need of therapeutic treatment comprising administering to said mammal (a) a therapeutically effective amount of a first composition comprising a balanced PC composition; and (b) a therapeutically effective amount of a second composition comprising one or more cannabinoids, a natural or synthetic derivative thereof, or a salt thereof; wherein said first composition and said second composition are each optionally and independently administered together with a pharmaceutically acceptable carrier or diluent, and wherein said therapeutic treatment is prevention, treatment or amelioration of one or more signs or symptoms of Alzheimer's disease.

In certain embodiments, the one or more signs or symptoms of Alzheimer's disease that are reduced or ameliorated include impairment of short term memory, impairment of abstract thinking, impairment of judgment, impairment of language skills, dementia, and mood changes, or any combination thereof.

In yet another aspect, the present invention is directed to compositions and methods for treating atherosclerosis and related diseases and disorders in a subject in need thereof as disclosed in Applicant's U.S. Provisional Application No. 61/969,063, filed Mar. 21, 2014, entitled Compositions and Methods for Treating Atherosclerosis, and assigned to BodyBio Inc., the entire contents of which are incorporated herein by reference.

Thus, in one embodiment, this invention is directed to composition comprising a first composition for use with a second composition for achieving an anti-atherosclerotic effect in a subject, wherein said first composition comprises a therapeutically effective amount of a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said antiatherosclerotic effect is manifested by a slowing of the progression of atherosclerotic plaques, wherein said progression of atherosclerotic plaques is slowed in coronary arteries, carotid arteries, or the peripheral arterial system or any combination thereof In another embodiment, the antiatherosclerotic effect is manifested by a regression of atherosclerotic plaques, wherein the regression of atherosclerotic plaques occurs in coronary arteries, carotid arteries, or the peripheral arterial system, or any combination thereof.

In another aspect of the present invention, methods are provided for treating a subject at risk for developing symptoms of diseases related to impairment of development and activities of cells and tissues in order to delay the onset of the one or more of the aforementioned underlying symptoms related to atherosclerosis. The prevention, treatment and/or amelioration of one or more of the aforementioned symptoms related to seizure need not be complete, so long as at least one symptom of the disease is prevented, treated or ameliorated.

In one embodiment, this invention is also directed to a method for treating a subject which has been diagnosed as suffering from atherosclerosis and who is in need of therapeutic treatment comprising administering to said mammal (a) a therapeutically effective amount of a first composition comprising a balanced PC composition; and (b) a therapeutically effective amount of a second composition comprising one or more cannabinoids, a natural or synthetic derivative thereof, or a salt thereof; wherein said first composition and said second composition are each optionally and independently administered together with a pharmaceutically acceptable carrier or diluent, and wherein said therapeutic treatment is prevention, treatment or amelioration of one or more symptoms of atherosclerosis.

In another aspect, the present invention is directed to compositions and methods for treating depression and related diseases and disorders in a subject in need thereof as disclosed in Applicant's U.S. Provisional Application No. 61/969,069, filed Mar. 21, 2014, entitled Compositions and Methods for Treating Depression, and assigned to BodyBio Inc., the entire contents of which are incorporated herein by reference.

Thus, in one embodiment, this invention is directed to composition comprising a first composition for use with a second composition for achieving an anti-depression effect in a subject, wherein said first composition comprises a therapeutically effective amount of a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-depression effect is manifested by a reduction or amelioration of the progression of signs or symptoms associated with depression including depressed mood, irritability, instability of mood, and/or changes in mood, stress, hormonal mood swings (e.g., during pregnancy, during post-partum, during puberty, during menopause or are a result of a Premenstrual Dysphoric Disorder or related condition), impairment of short term memory, impairment of abstract thinking, impairment of judgment, impairment of language skills, and depression-related dementia, or any combination thereof.

In another aspect of the present invention, methods are provided for treating a subject at risk for developing symptoms of diseases related to impairment of development and activities of cells and tissues in order to delay the onset of the one or more of the aforementioned underlying symptoms related to depression. The prevention, treatment and/or amelioration of one or more of the aforementioned symptoms related to depression need not be complete, so long as at least one symptom of the disease is prevented, treated or ameliorated.

In one embodiment, this invention is also directed to a method for treating a subject which has been diagnosed as suffering from depression or a related disease or disorder and who is in need of therapeutic treatment comprising administering to said subject (a) a therapeutically effective amount of a first composition comprising a balanced PC composition; and (b) a therapeutically effective amount of a second composition comprising one or more cannabinoids, a natural or synthetic derivative thereof, or a salt thereof; wherein said first composition and said second composition are each optionally and independently administered together with a pharmaceutically acceptable carrier or diluent, and wherein said therapeutic treatment is prevention, treatment or amelioration of one or more signs or symptoms of depression.

In certain embodiments, the one or more signs or symptoms of depression that are reduced or ameliorated include depressed mood, irritability, instability of mood, and/or changes in mood, stress, hormonal mood swings (e.g., during pregnancy, during post-partum, during puberty, during menopause or are a result of a Premenstrual Dysphoric Disorder or related condition), impairment of short term memory, impairment of abstract thinking, impairment of judgment, impairment of language skills, and depression-related dementia, or any combination thereof.

In another embodiment, this invention is directed to composition comprising a first composition for use with a second composition for achieving an anti-seizure effect, an anti-alzheimer's effect, an anti-atherosclerosis effect, anti-depression effect in a subject, or any combination thereof, wherein said first composition comprises a therapeutically effective amount of a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-seizure effect, anti-alzheimer's effect, anti-atherosclerosis effect, anti-depression effect, or any combination thereof, is manifested by a reduction or amelioration of the progression of the signs or symptoms associated with seizure, alzheimer's, atherosclerosis, depression, as described supra, or any combination thereof.

In another embodiment, this invention is also directed to a method for treating a subject which has been diagnosed as suffering from seizure, alzheimer's, atherosclerosis, depression or a related disease or disorder, or any combination thereof, and who is in need of therapeutic treatment comprising administering to said subject (a) a therapeutically effective amount of a first composition comprising a balanced PC composition; and (b) a therapeutically effective amount of a second composition comprising one or more cannabinoids, a natural or synthetic derivative thereof, or a salt thereof; wherein said first composition and said second composition are each optionally and independently administered together with a pharmaceutically acceptable carrier or diluent, and wherein said therapeutic treatment is prevention, treatment or amelioration of one or more signs or symptoms of seizure, alzheimer's atherosclerosis, depression, as recited supra, or any combination thereof.

In each of the aforementioned methods, the one or more cannabinoids comprise natural or synthetic variants of cannabinoids and include for example and not by way of limitation, those Cannabis-Derived Cannabinoids comprising Cannabinoids obtained from Cannabis indica plant including, for example, and not by way of limitation, Cannabidiol (CBD), Cannabinol (CBN), Cannabigerol (CBG); Cannabichromene (CBC); Cannabicyclol (CBL); Cannabivarin (CBV); Tetrahydrocannabivarin (THCV); Cannabidivarin (CBDV); Cannabichromevarin (CBCV); Cannabigerovarin (CBGV); Cannabigerol Monomethyl Ether (CBGM); and Tetrahydrocannabinol (THC), other Phytocannabinoids comprising those cannabinoids from several other several plant species besides cannabis, including, for example, and not by way of limitation, Echinacea purpurea, Echinacea angustifolia, Echinacea pallida, Acmella oleracea, Helichrysum umbraculigerum, and Radula marginata, as well as Synthetic Cannabinoids including, for example, and not by way of limitation, Dronabinol (Marinol) (Δ9-tetrahydrocannabinol (THC)), Nabilone (Cesamet), Sativex, and Rimonabant (SR141716).

In another aspect, a kit is provided for the pharmaceutical composition comprising: a) a first composition comprising a balanced PC composition; b) a second composition comprising one or more cannabinoids, an isolated natural or synthetic derivative thereof, or salt thereof; and c) instructions for the use of the first and second active compositions and the additional constituents of the kit.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

III. DETAILED DESCRIPTION OF THE INVENTION

Reference now will be made in detail to embodiments of the invention. It will be apparent to those skilled in the art that various modifications and variations can be made in the present invention without departing from the scope or spirit of the invention. For instance, features illustrated or described as part of one embodiment, can be used on another embodiment to yield a still further embodiment.

In general, the present invention is directed to compositions and methods related to a combination therapy that prevents, ameliorates and/or treats symptoms of diseases and disorders related to imbalance of fatty acids and developmental imbalance and dysfunction of cells and tissues, as applied to a wide spectrum of diseases and disorders, listed infra, through administration of a combination therapy comprising a first composition comprising a balanced PC composition in combination with a second composition comprising one or more cannabinoids.

The combination therapy of the present invention has unexpectedly completely circumvented the known deleterious side effects associated with the higher dose administration of cannabinoids by co-administration of a balanced PC composition and one or more cannabinoids, which in turn increases the bioavailability of this drug and its adsorption and passage through cell membranes and the blood brain barrier.

Cannabinoids such as, for example, cannabis or cannabidiol have been shown to be effective for modulation of tissue regeneration and development. There are, however, many side effects associated with cannabis and especially to the higher dosages of cannabis. Only about 1% of cannabis is reported to pass the blood brain barrier when administered alone intravenously.

By reducing or preventing the one or more side effects of the use of cannabinoids alone, the present invention provides a combination therapy of one or more cannabinoids with a balanced PC composition, wherein the overall therapeutic benefits described infra are increased considerably. Furthermore, the reduction or prevention of the side effects of cannabinoid use when administered in combination with a balanced PC composition provides an unexpected synergistic benefit.

The unexpected synergistic effects of the balanced PC composition cannabinoid combination therapy of the present invention include, for example, and not by way of limitation, i) reducing the oxidative stress of free radicals and increasing cellular homeostasis resulting from synergistically increasing the bioavailability of one or more cannabinoids; ii) inhibiting the formation of cholesteryl esters derived from LDL or other synthesis and increasing efflux of cholesterol from the cells by decreasing available cholesterol for esterification as a result of synergistically increasing the bioavailability of both endogenous and exogenous cannabinoids; iii) inhibiting the progression of atherosclerotic plaque and significantly reducing arterial plaque through modulation and synergistically increasing the bioavailability of both endogenous and exogenous cannabinoids; and iv) acting as a smooth muscle relaxant, relaxing arterial walls (vasodilatation), lowering blood pressure, and increasing blood flow and circulation by synergistically increasing the bioavailability of cannabinoids.

In general, a balanced PC composition of the present invention provides the following beneficial characteristics: i) enhanced PC concentration; ii) improved solubility and stability of PC; iii) Improved bioavailability of PC; iv)

improved targeting cell membrane capability in vivo and hence enhanced immunological benefit (a balanced PC composition has an enhanced glycoprotein concentration and hence increased capability to provide additional receptors via attachment to cell membranes in vivo); v) having a reduced concentration of integral carbohydrates including glycolipids, galactose, etc.; vi) having a reduced concentration of undesirable lipids including, for example, sphingomyelin; vii) having an improved concentration of the essential fatty acids and a balanced ratio of linoleic acid and alpha linolenic acid (in an approximate 4:1 ratio); and viii) having a range of beneficial minerals and electrolytes in a specific concentration range; and xi) having an improved ability for liposome mediated-transport of drugs or any combination thereof. These balanced PC composition benefits synergistically combine together with the one or more cannabinoids in the balanced PC cannabinoid composition combination therapy utilized in the compositions and methods of the present invention to provide one or more of the therapeutic benefits described herein.

In one embodiment, the balanced PC composition cannabinoid compositions and methods prepared according to the present invention provide a suspension of liposomes containing substantially more phosphatidylcholine than the available competing phosphatidyl products.

In another embodiment, the liposomes produced by the methods of the present invention are small unilamellar vesicles (SUVs) having sizes predominantly between 0.02 and 0.1 microns, and are composed predominantly or exclusively of a balanced PC composition with the one or more cannabinoids entrapped there within.

Without intending to be limited to a particular mechanism of action, it is believed that the administration of a balanced PC composition in combination with one or more exogenous cannabinoids serves to synergistically regulate and promote the aforementioned physiological homeostasis in the endocannabinoid system by leading to a decrease in the relative sphingomyelin to phosphatidylcholine mass ratio which in turn synergistically allows the endogenous cannabinoid system to modulate the severity and/or duration of seizure, Alzheimer's disease, atherosclerosis, and/or depression through activation of the CB1 receptor.

Components of the Composition of the Combination Therapy

1. Components of Balanced PC Composition
1.1 Phosphatidylcholine

Phosphatidylcholine (PC) is the predominant phospholipid of all cell membranes and of the circulating blood lipoproteins. Of the tens of thousands of molecules that make up the life of a cell, Phosphatidylcholine (PC) stands apart; probably the most important one of all. PC is the main lipid constituent of the lipoprotein particles circulating in the blood and the preferred precursor for certain phospholipids and other biologically important molecules. PC also provides antioxidant protection in vivo. In animal and human studies, PC protected against a variety of chemical toxins and pharmaceutical adverse effects.

Chemically, PC is a glycerophospholipid that is built on glycerol (CH2OH—CHOH—CH2OH) and substituted at all three carbons. Carbons 1 and 2 are substituted by fatty acids and carbon 3 by phosphorylcholine. Simplistically, the PC molecule consists of a head-group (phosphorylcholine), a middle piece (glycerol), and two tails (the fatty acids, which vary). Variations in the fatty acids in the tails account for the great variety of PC molecular species in human tissues.

In vivo, PC is produced via two major pathways. In the predominant pathway, two fatty acids (acyl "tails") are added to glycerol phosphate (the "middle piece"), to generate phosphatidic acid (PA) that is converted to diacylglycerol, after which phosphocholine (the "head-group") is added on from CDP-choline. The second, minor pathway is phosphatidylethanolamine (PE) methylation, the PEMT pathway, in which the phospholipid PE has three methyl groups added to its ethanolamine head-group, thereby converting it into PC.

In one embodiment, the PC component of the balanced PC composition cannabinoid combination therapy of the present invention may be derived from any and all lecithin-based raw materials, for which the phosphatides have been rendered water soluble by one of the many previously published fluidizing methods, for example, Short, U.S. Pat. No. 4,221,731 1980, Flider, U.S. Pat. No. 4,399,224 1983, the entire disclosures of each of which are specifically incorporated by reference herein, and those commercial suppliers of raw lecithin such as, for example, and not by way of limitation, Archer Daniels Midland (ADM), Cargill, Bunge, Solae, American Lecithin, or any plant lecithin or animal lecithin including for example, and not by way of limitation, egg, or any combination thereof.

In another embodiment, the PC component of the balanced PC composition cannabinoid combination therapy comprises phosphatidylcholine derived from soy.

In another embodiment, the first composition of the present invention is a balanced PC composition which is specifically available from BodyBio Inc. (referred to hereinafter as "BodyBio PC", "BodyBio balanced PC" or "balanced PC"). The concentration of PC in BodyBio PC for administration ranges from about 100 mg to about 10,000 mg. In one embodiment, the concentration range of PC is from about 200 mg to about 5000 mg. In another embodiment, the concentration range of PC is from about 300 mg to about 3000 mg. In a preferred embodiment of the invention, the concentration range of PC is from about 500 mg to about 1000 mg.

In one embodiment, the total amount of phospholipids in BodyBio PC is about 61%, which is about 9% higher than competitive PC products (i.e., approximately 61% versus about 52%). In one embodiment, total amount of phosphatidylcholine in BodyBio PC is approximately 29%, which is about 11-16% higher than competitive PC products such as for example, and not by way of limitation, that found with lecithin supplied by Dupont and ADM (i.e., about 29% versus about 18%). The percentages recited herein for the differences between BodyBio PC and competitive PC products are approximations only and are thus intended to include percentages that are up to 10% lower or 10% higher than the recited value, and all integer values there between.

In one embodiment, for example, and not by way of limitation, the fatty acids and phospholipid concentration in the intermediate phosphatidylcholine compound is presented below (including any combinations thereof). These percentage values provided below represent a non-limiting example of fatty acid content and of the various phospholipids found in the composition. The percentages recited herein are approximate and are intended to include percentages that are up to 10% lower or 10% higher than the recited value.

Fatty Acid Content:
C16.0 16.1%
C16.1 0.1%
C18.0 4.1%
C18.1 10.0%
C18.2 55.30% (omega 6)
C18.3 14.0% (omega 3)
C22.0 0.4%

Phospholipids:
Phosphotidylcholine (PC): about 29%
Phosphotidylethanolamine (PE): about 16%
Phosphatidyl inositol (PI): about 9%
Phosphatidic Acid (PA): about 4%
Phosphatidylglycerol (PG): about 1%
Total Phospholipids about 61%

BodyBio PC contains a ratio of about 4 parts linoleic acid to about 1 part alpha linolenic acid. Most lecithin produced from soy has an essential fatty acid ratio of approximately 10-12:1.

BodyBio balanced PC is composed of phosphatides that are amphiphilic and automatically form bilipid membranes (liposomes) or unilipid membranes (micelles). Lecithin may contain the desired health providing phosphatides, however, in contrast to BodyBio balanced PC, the phospholipids derived from lecithin are generally oil based, which make them only suitable as an emulsifying agent for foods and cosmetics. Oil-based phosphatides are not amphiphilic, they have lost the necessary hydrophobic reaction to form a liposomal membrane and thus are incapable of integration into cell membranes and add to internal nutritional support system.

The increased level of available phospholipids in the balanced PC composition of the present invention is a significant improvement over the competitive PC products. The balanced PC compositions of the present invention have the unique advantage of containing phosphatidyl ethanolamine (PE), which has recently been found to be a necessary phospholipid in the membranes of mitochondria for the production of energy.

Thus, in one embodiment of the present invention, the balanced PC composition of the present invention comprises Phosphotidylcholine (PC), Phosphotidylethanolamine (PE), Phosphatidyl inositol (PI), Phosphatidic Acid (PA), Essential Fatty Acids comprising C18.2 (omega 6) (linoleic acid) C18.3 (omega 3) (alpha linolenic acid) (in an approximate 4:1 ratio for the essential fatty acids or EFAs), or any combination thereof.

Mitochondrial membranes are enriched in phospholipids and proteins that are required for mitochondrial biogenesis and for maintenance of mitochondrial morphology and the tubular network. The two non-bilayer forming mitochondrial phospholipids cardiolipin (CL) (CL3) and phosphatidylethanolamine (PE) are required to maintain tubular mitochondrial morphology and are known to have overlapping functions in mitochondrial fusion. Although cells lacking CL or mitochondrial PE are viable, the loss of both phospholipids is lethal.

2. Cannabinoids for Use in the Second Composition

The compositions of the combination therapy of the present invention include as the second composition one or more cannabinoids, an isolated natural or synthetic derivative thereof, or salt thereof. Cannabinoids are a heteromorphic group of chemicals that act on cannabinoid receptors on cells that repress neurotransmitter release in the brain. These receptor proteins include the endocannabinoids (produced naturally in the body by humans and animals), the phytocannabinoids (found in *cannabis* and some other plants), and synthetic cannabinoids (manufactured chemically). The most notable cannabinoid is the phytocannabinoid Δ9-tetrahydrocannabinol (THC), the primary psychoactive compound of *cannabis*. Cannabidiol (CBD) is another major constituent of the plant, representing up to 40% in extracts of the plant resin. There are at least 85 different cannabinoids isolated from *cannabis*, exhibiting varied effects. Synthetic cannabinoids encompass a variety of distinct chemical classes: the classical cannabinoids structurally related to THC, the nonclassical cannabinoids (cannabimimetics) including the aminoalkylindoles, 1, 5-diarylpyrazoles, quinolines, and arylsulphonamides, as well as eicosanoids related to the endocannabinoids.

Cannabinoids according to this invention can either be exogenic or endogenic in origin. Exogenic cannabinoids can be both natural, (i.e. Phytocannabinoids derived from the *cannabis* plant itself) and synthetic (i.e. Marinol, Sativex, etc.) These exogenic cannabinoids can be both binding, aka agonists (i.e. THC the main psychoactive compound) and non-binding, aka antagonists (i.e., the non-psychoactive cannabinoids CBD, CBN, CBG, etc.) to endogenous cannabinoid receptors in vivo. Endogenic cannabinoids (i.e. Anandamide, 2-AG, etc.) and endogenous receptors sites (i.e. CB1 and CB2) are found throughout the body and regulate homeostasis in a wide variety of physiological and neurological functions from birth till death. Endocannabinoids are found in the human placenta and even breast milk and are essential to all the body's regulatory functions.

Endocannabinoids are lipid derived mediators which can be activated, stored, and synthesized from the cell membranes phospholipid's bilayer through multiple pathways, although complete understanding of the transport system needs further study. Endocannabinoid production can be increased by the introduction of extracellular stimuli (i.e., the ingestion or introduction of exogenous cannabinoids). The phospholipid bilayer, along with its many other functions, plays a central role in the Endocannabinoid System. A healthy phospholipid bilayer is therefore essential to a healthy Endocannabinoid system (ECS) and vice versa: the phospholipid bilayer and the ECS work together synergistically to regulate and promote physiological homeostasis. The ECS and its regulatory processes are extremely sensitive to the quality and structure of the phospholipid bilayer. This relationship and the synergistic effects thereto are enhanced and exploited by using the balanced PC cannabinoid combination therapeutic treatments of the invention as described herein to achieve a further synergistic effect which is much greater than the additive value expected by combination of a balanced PC composition and cannabinoids.

What follows is a non-limiting listing of the cannabinoids that may be used in the combination therapy compositions and methods of the present invention.

2.1 *Cannabis*-Derived Cannabinoids 2.1.1 *Cannabis, Sativa, Indica* Plant Ruderalis and Hybrids Thereof The *Cannabis* plant, a genus of dioeciously flowering plants, has been divided into three distinct species: *Cannabis Sativa, Cannabis Indica*, and *Cannabis Ruderalis*. Phytocannabinoids (i.e., THC, CBD, CBN, CBG, etc.) can be extracted through various methods and have been used in medicinal compositions for thousands of years by many different cultures around the world for a wide range of symptoms and ailments.

The classical cannabinoids are concentrated in a viscous resin produced in structures known as glandular trichomes. At least 85 different cannabinoids have been isolated from the *Cannabis* plant. The best studied cannabinoids include tetrahydrocannabinol (THC), cannabidiol (CBD) and cannabinol (CBN).

Despite the huge variety of marijuana available, almost all ultimately come from two *cannabis* family species. These two essential species are known as *Cannabis sativa* and *Cannabis Indica* and they differ fundamentally in their chemical composition and medical applications. *Cannabis Ruderalis* a.k.a. industrial hemp is the third species and interest in this species is gaining momentum at the moment because it is high in the non-psychoactive cannabinoid CBD and contains only trace amounts of 1% or less the psychoactive cannabinoid.

2.2.1 Types of Cannabinoids

All classes derive from cannabigerol-type compounds and differ mainly in the way this precursor is cyclized. The classical cannabinoids are derived from their respective 2-carboxylic acids (2-COOH) by decarboxylation (catalyzed by heat, light, or alkaline conditions) include the following: CBG (Cannabigerol); CBC (Cannabichromene); CBL (Cannabicyclol); CBV (Cannabivarin); THCV (Tetrahydrocannabivarin); CBDV (Cannabidivarin); CBCV (Cannabichromevarin); CBGV (Cannabigerovarin); CBGM (Cannabigerol Monomethyl Ether); and Tetrahydrocannabinol 2.2.2 Tetrahydrocannabinol Tetrahydrocannabinol (THC) is the primary psychoactive component of the *Cannabis* plant. Delta-9-tetrahydrocannabinol ($\Delta$9-THC, THC) and delta-8-tetrahydrocannabinol ($\Delta$8-THC) mimic the action of anandamide, a neurotransmitter produced naturally in the body. These two THC's produce the effects associated with *cannabis* by binding to the CB1 cannabinoid receptors in the brain. THC appears to ease moderate pain (analgesic) and to be neuroprotective. Studies show THC reduces neuroinflammation and stimulates neurogenesis. THC has approximately equal affinity for the CB1 and CB2 receptors. Its effects are perceived to be more cerebral.

2.2.2.1 Sources of THC

The *Indica* and *Sativa* subspecies differ in their medicinal properties. *Sativa* strains produce more of a euphoric high, lifting the consumer's mood and therapeutically relieving stress. *Indica* strains relax muscle and work as general analgesics, also helping with sleep. A cancer patient hoping to relieve the pain from chemotherapy would benefit greatly from the effects of an *Indica* plant bud, whereas an individual dealing with depression would better benefit from an extract from *Sativa* plant. *Sativa*'s has low or no CBD levels. *Indica*'s chemical profile shows a more balanced mix, with moderate THC levels and higher levels of CBD. Differences in the chemical composition of *Cannabis* varieties may produce different effects in humans. Synthetic THC, called dronabinol (Marinol), does not contain CBD, CBN, or other cannabinoids, which is one reason why its pharmacological effects may differ significantly from those of natural *Cannabis*. Hybridization and crosses of all three exists and are of particular interest, especially if breeding for certain cannabinoid percentage profiles. (i.e., High THC/High CBD, Low THC/High CBD).

2.2.3 Cannabidiol

Cannabidiol (CBD) is not psychoactive, and was thought not to affect the psychoactivity of THC. However, recent evidence shows that smokers of *cannabis* with a higher CBD/THC ratio were less likely to experience schizophrenia-like symptoms. Cannabidiol has little affinity for CB1 and CB2 receptors but acts as an indirect antagonist of cannabinoid agonists. It is an antagonist at the putative new cannabinoid receptor, GPR55, a GPCR expressed in the caudate nucleus and putamen. Cannabidiol has also been shown to act as a 5-HT1A receptor agonist, an action that is involved in its antidepressant, anxiolytic, and neuroprotective effects. It appears to relieve convulsion, inflammation, anxiety, and nausea. CBD has a greater affinity for the CB2 receptor than for the CB1 receptor. CBD shares a precursor with THC and is the main cannabinoid in low-THC *Cannabis* strains. CBD apparently plays a role in preventing the short-term memory loss associated with THC in mammals.

2.2.4 Cannabinol

Cannabinol (CBN) is the primary product of THC degradation, and there is usually little of it in a fresh plant. CBN content increases as THC degrades in storage, and with exposure to light and air. It is only mildly psychoactive. Its affinity to the CB2 receptor is higher than for the CB1 receptor.

2.2.5 Cannabigerol

Cannabigerol (CBG) is non-psychotomimetic but still affects the overall effects of *Cannabis*. It acts as an $\alpha$2-adrenergic receptor agonist, 5-HT1A receptor antagonist, and CB1 receptor antagonist. It also binds to the CB2 receptor.

2.2.6 Tetrahydrocannabivarin

Tetrahydrocannabivarin (THCV) is prevalent in certain central Asian and southern African strains of *Cannabis*. It is an antagonist of THC at CB1 receptors and attenuates the psychoactive effects of THC.

2.2.7 Cannabidivarin

Although cannabidivarin (CBDV) is usually a minor constituent of the cannabinoid profile, enhanced levels of CBDV have been reported in feral *cannabis* plants from the northwest Himalayas, and in hashish from Nepal.

2.2.8 Cannabichromene

Cannabichromene (CBC) is non-psychoactive and does not affect the psychoactivity of THC. Cannabichromene is more common in tropical *cannabis* varieties. Effects include anti-inflammatory and analgesic. THC It is found in nearly all tissues in a wide range of animals. Two analogs ofanandamide, 7,10,13,16-docosatetraenoylethanolamide and "homo"-y-linolenoylethanolamine, have similar pharmacology. All of these are members of a family of signaling lipids called "N"-acylethanolamines, which also includes the non-cannabimimetic palmitoylethanolamide and oleoylethanolamine, which possess anti-inflammatory and orexigenic effects, respectively. Many "N"-acylethanolamines have also been identified in plant seeds and in molluscs.

2.2.9 Cannabicyclol

Cannabicyclol (CBL) is a non-psychoactive cannabinoid found in the *cannabis* species. CBL is a degradative product like Cannabinol. Light converts Cannabichromene to CBL and it contains 16 stereoisomer.

2.2.10 Cannabivarin

Cannabivarin (CBV) is a non-psychoactive cannabinoid found in minor amounts in *cannabis* plant. It is an analog of cannabinol (CBN). Cannabivarin is an oxidation product of Tetrahydrocannabivarin (THCV)

2.3 Other Phytocannabinoids

The compositions of the present invention may also utilize phytocannabinoids from several other several plant species besides *cannabis*. These include *Echinacea purpurea, Echinacea angustifolia, Echinacea pallida, Acmella oleracea, Helichrysum umbraculigerum*, and *Radula marginata*. The best known cannabinoids that are not derived from *Cannabis* are the lipophilic alkamides (alkylamides) from *Echinacea* species. At least 25 different alkylamides (dodeca-2E,4E,8Z,10E/Z-tetraenoic-acid-isobutylamides) have been identified, and some of them have shown affinities to the CB2-receptor. In *Echinacea* species, cannabinoids are found throughout the plant structure, but are most concentrated in the roots and flowers. Yangonin found in the Kava plant is a ligand on the CB1 receptor. Tea (*Camellia sinensis*) catechins have an affinity for human cannabinoid receptors. A wide spread dietary cannabinoid, beta-caryophyllene, a component from the essential oil of *cannabis* and other medicinal plants, has also been identified as a selective agonist of peripheral CB2-receptors, in vivo.

2.4 Synthetic Cannabinoids

In addition to the natural cannabinoids described above for use in the second composition of the present invention, synthetic cannabinoids may also be used. One of ordinary skill in the art can readily synthesize numerous synthetic cannabinoids for use in the compositions and methods of the present invention. Non-limiting representative examples of such synthetic cannabinoids include, for example, Dronabinol (Marinol) (Δ9-tetrahydrocannabinol (THC)), used as an appetite stimulant, anti-emetic, and analgesic; Nabilone (Cesamet), a synthetic cannabinoid and an analog of Marinol; Sativex, a cannabinoid extract oral spray containing THC, CBD, and other cannabinoids used for neuropathic pain and spasticity in 22 countries including England, Canada and Spain; and Rimonabant (SR141716), a selective cannabinoid (CB1) receptor inverse agonist once used as an anti-obesity drug under the proprietary name Acomplia.

2.5 Endocannabinoids

The endogenous cannabinoid system (ECS) is perhaps the most important physiological system involved in establishing and maintaining human health through homeostasis. Found throughout the body the ECS endocannabinoids serve as intercellular lipid messengers. Although in this intracellular signaling role they are similar to the well-known monoamine neurotransmitters, such as acetylcholine and dopamine, endocannabinoids differ in numerous ways from them. For instance, they use retrograde signaling. Non limiting examples of endocannabinoids that may be modulated by the compositions and methods of the present invention include, for example, those endocannabinoids listed below.

2.5.1 N-Arachidonoylethanolamine

N-arachidonoylethanolamine (AEA), also known as Anandamide, is an endogenous cannabinoid neurotransmitter. It is synthesized from N-arachidonoyl phosphatidylethanolamine by multiple pathways. It is degraded primarily by the fatty acid amide hydrolase (FAAH) enzyme, which converts anandamide into ethanolamine and arachidonic acid. Inhibitors of FAAH lead to elevated anandamide levels and are being pursued for therapeutic use and treatments. Anandamide's effects can be either central, in the brain, or peripheral, in other parts of the body. These effects are mediated by the CB1 receptors in the CNS, and the CB2 receptors in the periphery, which is involved in homeostasis and functions of the immune system.

2.5.2 2-arachidonoyl glycerol (2-AG)

Another endocannabinoid, 2-arachidonoyl glycerol, binds to both the CB1 and CB2 receptors with similar affinity, acting as a full agonist at both, and there is some controversy over whether 2-AG rather than anandamide is chiefly responsible for endocannabinoid signaling in vivo. In particular, one in vitro study suggests that 2-AG is capable of stimulating higher G-protein activation than anandamide, although the physiological implications of this finding are not yet known.

2.5.3 2-Arachidonyl Glyceryl Ether (Noladin Ether)

Endocannabinoid, 2-arachidonyl glyceryl ether (noladin ether), is isolated from porcine brain. Previously, it had been synthesized as a stable analog of 2-AG; indeed, some controversy remains over its classification as an endocannabinoid, as another group failed to detect the substance at "any appreciable amount" in the brains of several different mammalian species. Noladin ether binds to the CB1 cannabinoid receptor ("K" i=21.2 nmol/L) and causes sedation, hypothermia, intestinal immobility, and mild antinociception in mice. It binds primarily to the CB1 receptor, and only weakly to the CB2 receptor. Like anandamide, NADA is also an agonist for the vanilloid receptor subtype 1 (TRPV1), a member of the vanilloid receptor family.

2.5.4 Virodhamine (OAE)

Virodhamine, or "0"-arachidonoyl-ethanolamine (OAE), is a full agonist at CB2 and a partial agonist at CB1, although it behaves as a CB1 antagonist "in vivo". In rats, Virodhamine was found to be present at comparable or slightly lower concentrations than anandamide in the brain, but 2- to 9-fold higher concentrations peripherally.

2.5.5 Function of Endocannabinoids

Endocannabinoids serve as intercellular 'lipid messengers', signaling molecules that are released from one cell and activate the cannabinoid receptors present on other nearby cells. Although in this intercellular signaling role they are similar to the well-known monoamine neurotransmitters, such as acetylcholine and dopamine, endocannabinoids differ in numerous ways from them. For instance, they use retrograde signaling. Furthermore, endocannabinoids are lipophilic molecules that are not very soluble in water. They are not stored in vesicles, and exist as integral constituents of the membrane bilayers that make up cells. They are believed to be synthesized 'on-demand' rather than made and stored for later use. The mechanisms and enzymes underlying the biosynthesis of endocannabinoids remain elusive and continue to be an area of active research. The endocannabinoid 2-AG has been found in bovine and human maternal milk.

2.5.6 Retrograde Signal

Conventional neurotransmitters are released from a 'presynaptic' cell and activate appropriate receptors on a 'postsynaptic' cell, where presynaptic and postsynaptic designate the sending and receiving sides of a synapse, respectively. Endocannabinoids, on the other hand, are described as retrograde transmitters because they most commonly travel 'backwards' against the usual synaptic transmitter flow. They are, in effect, released from the postsynaptic cell and act on the presynaptic cell, where the target receptors are densely concentrated on axonal terminals in the zones from which conventional neurotransmitters are released. Activation of cannabinoid receptors temporarily reduces the amount of conventional neurotransmitter released. This endocannabinoid mediated system permits the postsynaptic cell to control its own incoming synaptic traffic. The ultimate effect on the endocannabinoid-releasing cell depends on the nature of the conventional transmitter being controlled. For instance, when the release of the inhibitory transmitter GABA is reduced, the net effect is an increase in the excitability of the endocannabinoid-releasing cell.

3. Compositions and Therapeutic Methods

The novel combination of a balanced PC composition with one or more cannabinoids, which are synergistic when used in combination, results in easy delivery of and passage of a balanced PC composition and cannabinoids through the cell membrane and the blood brain barrier to support tissue regeneration, to inhibit the inflammatory reactions and to promote cerebral reperfusion.

Thus, in one embodiment, this invention is directed to a first composition for use with a second composition for ameliorating or treating one or more symptoms of seizures, Alzheimer's, depression, and atherosclerosis in a subject, wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In one embodiment, treatment of symptoms of seizure is manifested by a slowing of the progression of one or more of the aforementioned symptoms or effects of seizures listed supra.

In another embodiment, this invention is directed to a first composition for use with a second composition for achieving an anti-epileptic effect in a subject suffering from epilepsy, refractory, partial-complex epilepsy, temporal lobe epilepsy, or a combination thereof, wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, the anti-epileptic effect is manifested by a slowing of the progression of one or more symptoms or effects of epilepsy including, for example, and not by way of limitation, staring spells, loss of alertness, violent shaking, strange sensation such as tingling, smelling an odor that is not present, or emotional changes prior to each seizure (aura), depression, cognitive decline, death, or any combination thereof.

In yet another embodiment, this invention is directed to a first composition for use with a second composition for achieving an anti-"Grand Mal" or generalized tonic-clonic effect in a subject suffering from Grand Mal" or generalized tonic-clonic, wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, the anti-"Grand Mal" or generalized tonic-clonic effect is manifested by a slowing of the progression of one or more symptoms or effects of seizure including, for example, and not by way of limitation, muscle stiffness and rigidity (the "tonic" phase), unconsciousness, convulsions, muscle rigidity, repetitive, jerking movements, repetitive, rhythmic jerks on both sides of the body, violent jerking (the "clonic" phase), injuries and accidents tongue biting, urinary incontinence, deep sleep (the "postictal" or after-seizure phase), or any combination thereof.

In yet another embodiment, this invention is also directed to a first composition for use with a second composition for achieving an anti-absence seizure effect in a subject suffering from absence seizure, wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-absence seizure effect is manifested by a slowing of the progression of one or more symptoms or effects of absence seizure including, for example, and not by way of limitation, short loss of consciousness (just a few seconds) with few or no symptoms, interruption of daily activity, blank stares, "losing time", or any combination thereof.

In yet another embodiment, this invention is also directed to a first composition for use with a second composition for achieving an anti-myoclonic sporadic seizures (isolated) effect in a subject at risk of suffering from myoclonic sporadic seizures, wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-myoclonic sporadic seizure effect is manifested by a slowing of the progression of one or more symptoms or effects of myoclonic sporadic seizures including, for example, and not by way of limitation, jerking movements usually on both sides of the body, dropping or involuntarily throwing objects, or any combination thereof.

In yet another embodiment, this invention is also directed to a first composition for use with a second composition for achieving an anti-atonic seizures effect in a subject at risk of suffering from atonic seizures, wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-atonic seizure effect is manifested by a slowing of the progression of one or more symptoms or effects of atonic seizures including, for example, and not by way of limitation, a sudden and general loss of muscle tone, particularly in the arms and legs, falling, or any combination thereof.

In yet another embodiment, this invention is also directed to a first composition for use with a second composition for achieving an anti-simple partial seizures comprising focus, simple (awareness retained), simple motor, simple sensory, and simple psychological seizures effect in a subject suffering from the one or more of the aforementioned seizures, wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-simple partial seizure effect is manifested by a slowing of the progression of one or more symptoms or effects of simple partial seizure including, for example, and not by way of limitation, motor symptoms such as jerking, muscle rigidity, spasms, head-turning, sensory such as unusual sensations affecting either the vision, hearing, smell taste or touch, and psychological such as memory or emotional disturbances, or any combination thereof.

In yet another embodiment, this invention is also directed to a first composition for use with a second composition for achieving an anti-complex partial seizure (impairment of awareness) effect in a subject suffering from complex partial seizure, wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-complex partial seizure effect is manifested by a slowing of the progression of one or more symptoms or effects of complex partial seizure including, for example, and not by way of limitation, automatisms such as lip smacking, chewing, fidgeting, walking and other repetitive, involuntary but coordinated movements, or any combination thereof.

In yet another embodiment, this invention is also directed to a first composition for use with a second composition for achieving an anti-nocturnal seizure effect in a subject suffering from nocturnal seizure, wherein said first composition comprises (a) a therapeutically effective amount of a first composition comprising a balanced PC composition; and (b) a therapeutically effective amount of a second composition comprising one or more cannabinoids, a natural or synthetic derivative thereof, or a salt thereof, wherein said first composition and said second composition are each optionally and independently administered together with a pharmaceutically acceptable carrier or diluent.

In certain embodiments, said anti-nocturnal seizure effect is manifested by a slowing of the progression of one or more symptoms or effects of nocturnal seizure including, for example, and not by way of limitation, unusual differences upon awakening, headache, bed wetting, tongue biting, bone or joint injury, light-headedness, unusual mental behaviors, or any combination thereof.

In yet another embodiment, this invention is also directed to a method for treating a mammal which has been diagnosed as suffering from epilepsy, refractory, partial-complex epilepsy, temporal lobe epilepsy, seizure, Grand Mal or generalized tonic-clonic seizure, absence seizure, myoclonic sporadic seizures, atonic seizures, simple partial seizures comprising focus, simple (awareness is retained), simple motor, simple sensory, and simple psychological seizures, complex partial seizure, nocturnal seizure, or an combination thereof, and who is in need of therapeutic treatment comprising administering to said subject (a) a therapeutically effective amount of a first composition comprising a balanced PC composition; and (b) a therapeutically effective amount of a second composition comprising one or more cannabinoids, a natural or synthetic derivative thereof, or a salt thereof; wherein said first composition and said second composition are each optionally and independently administered together with a pharmaceutically acceptable carrier or diluent, and wherein said therapeutic treatment is prevention, treatment or amelioration of one or more of the aforementioned symptoms listed supra of epilepsy, seizure, Grand Mal or generalized tonic-clonic seizure, absence seizure, myoclonic sporadic seizures, atonic seizures, simple partial seizures comprising focus, simple (awareness retained), simple motor, simple sensory, and simple psychological seizures, complex partial seizures, nocturnal seizures, or any combination thereof.

Cannabinoids are medically efficacious for a variety of ailments and diseases. Specifically, cannabinoids are inhibitory to plaque formation, anti-oxidative in nature, impair the formation of cholesteryl esters, and act as vasodilators and smooth muscle relaxants in arterial walls; all of which are beneficial in treating symptoms of seizures and related diseases or disorders.

One of the main variables of membrane lipid composition is the quantitative relationships between sphingomyelin, phosphatidylcholine, and cholesterol, which are the main lipid components of the outer monolayer of mammalian plasma membranes. In most normal cells, there is a gradient of sphingomyelin from the cell boundary to cell center; its highest content is in the plasma membrane, the lowest in the inner mitochondrial membrane and the nuclear membrane. In the mammalian plasma membrane, the two choline-containing lipids, phosphatidylcholine and sphingomyelin, constitute more than 50% of the total phospholipid. Sphingomyelin content increases with aging, especially in tissues which have a relatively low phospholipid turnover. It also increases in several diseases, including atherosclerosis and certain types of cancer. For example, a 6-fold change in the sphingomyelin to phosphatidylcholine mole ratio takes place in the aorta and arterial wall during aging of normal humans. The change of this ratio in atherosclerosis is even more striking. In this disease, the sphingomyelin content can be as high as 70-80% of the total phospholipids in advanced aortic lesions.

In general, there is a strong positive correlation between the content of sphingomyelin and cholesterol in membranes. In addition, changes in the content of one are followed by comparable changes in the other. Indeed, it is still not clear how cells maintain the various lipid compositions in their different membranes despite the transfer and exchange of lipids among membranes in vivo. Pathological changes in sphingomyelin content might result from changes in the metabolism of the compound, i.e. increase in its rate of biosynthesis, reduction in its rate of degradation, or change in relative rate in phospholipid transfer in or out of cells. The change taking place in one membrane might remain localized or it may be propagated to other membranes of the cell by transfer of lipid. The relative content of phosphatidylcholine, sphingomyelin, and cholesterol appears to vary in different membrane systems and even within the same membrane under different conditions.

It is believed that oxidized lipids contribute to heart disease both by increasing deposition of calcium on the arterial wall, a major hallmark of atherosclerosis, and by interrupting blood flow, a major contributor to heart attack and sudden death. Oxidized cholesterol (oxysterols) enhances the production of sphingomyelin, which is the elevated phospholipid found in the cellular membranes of occluded coronary arteries. The increase of sphingomyelin content in the cell membrane enhances the interaction between the membrane and ionic calcium ($Ca^{2+}$), thereby increasing the risk of arterial calcification Without intending to be limited to a specific mechanism of action, one possible mechanism of action of the combination therapy of the present invention is through a cascade of one or more biochemical pathways that result in vasodilation and blood thinning, which in turn results in the significant reduction of blood lipids triglyceride, LDL and cholesterol. As a result of the administration of a balanced PC composition that has a blood thinning effect according to the present invention, the transport of one or more cannabinoids through cell membranes and the blood brain barrier is further facilitated. Because of the ease and efficiency of transport of cannabinoids that is caused by use of a balanced PC composition, the effective concentration of cannabinoids can be reduced by as much as about 10 fold to about 100 fold or more without reducing the therapeutic effectiveness of this drug.

The optimization of dosing of cannabinoids achieved with the compositions and methods of the present invention has tremendous clinical advantages in preventing the one or more side effects of use of cannabinoids including, for example, and not by away of limitation, those effects such as dysphoria, anxiety or panic, impairment of memory, reductions in psychomotor and cognitive performance, disordered perception of the passage of time, and euphoria, schizophrenic psychosis, tiredness, dizziness, tachycardia, orthostatic hypotension, dry mouth, reduced lacrimation, muscle relaxation, and increased appetite, potential irreversible cognitive impairments (albeit when used at high concentrations or when being used in children adolescents (particularly before puberty)) or any combination thereof that are known side effects of any cannabinoid-based therapy Thus, without intending to be limited to any specific mechanism of action, it is believed that subjects exhibiting symptoms or deleterious effects of seizures or related diseases or disorders or those subjects susceptible to those diseases or disorders have a heightened sphingomyelin to phosphatidylcholine relative ratio. Furthermore, the combination therapy of the invention results in a decrease in the relative sphingomyelin to phosphatidylcholine mass ratio. A non-limiting example of the beneficial sphingomyelin to phosphatidylcholine mass ratio achieved with the compositions and methods of the present invention is approximately 1.2-4.2. It is this decrease in the sphingomyelin to phosphatidylcholine ratio that serves to reduce or ameliorate the symptoms of seizures or related diseases or disorders.

The cannabinoids for use in the compositions and methods of the present invention are isolated endogenous cannabinoids, phytocannabinoids, recombinant cannabinoids, or a combination thereof, or can be administered exogenously, or may be administered through a combination of both endogenous and exogenous sources of cannabinoids. In general, administration of cannabinoids with a balanced PC composition increases the bioavailability of cannabinoids.

The compositions and methods of the present invention are beneficial in variety of bodily functions, including, by way of example and not limitation, reduction of calcification and plaque, the lowering bad cholesterol (LDL), reducing oxidative damages, and acting as a vasodilator and relaxant of smooth muscle cells, which would result in increasing blood flow and decreasing blood pressure.

4. Formulation and Modes of Administration

The terms "treat", "treated", "treating" and "treatment" are to be broadly understood as referring to any response to, or anticipation of, a medical condition in a mammal, particularly a human, and includes but is not limited to: (i) preventing the medical condition from occurring in a subject, which may or may not be predisposed to the condition, but has not yet been diagnosed with the condition and, accordingly, the treatment constitutes prophylactic treatment for the medical condition; (ii) inhibiting the medical condition, i.e., arresting, slowing or delaying the onset, development or progression of the medical condition; or (iii) relieving the medical condition, i.e., causing regression of the medical condition.

The term "therapeutically effective amount" or "therapeutically and/or prophylactically effective amount" as used herein refers to an amount of compound or agent that is sufficient to elicit the required or desired therapeutic and/or prophylactic response, as the particular treatment context may require.

It will be understood that a therapeutically and/or prophylactically effective amount of a drug for a subject is dependent inter alia on the body weight of the subject as well as other factors known to a person of ordinary skill in the art. A "subject" herein to which a therapeutic agent or composition thereof can be administered includes mammals such as a human subject of either sex and of any age, and also includes any nonhuman animal, particularly a domestic or companion animal, illustratively a cat, dog or a horse as well as laboratory animals such as guinea pigs.

As used herein, an "effective amount" of a composition is an amount sufficient to achieve a desired biological effect, in this case at least one of modulation of activity and/or development of cell populations and/or tissues that are targeted by the combination therapy of the invention. It is understood that the effective dosage will be dependent upon the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

As used herein, a "subject" is any mammal, in particular a primate, preferably a human, that 1) exhibits at least one symptom associated with impairment of tissue development and activity, or 2) and has been diagnosed with or is at the risk of developing a disease or disorder that is causes in impairment of tissue development and activity.

In a specific embodiment, the term "pharmaceutically acceptable" means approved by a regulatory agency of the Federal or a state government or listed in the U.S. Pharmacopcia or other generally recognized pharmacopcia for use in animals, and more particularly in humans.

The term "carrier" refers to a diluent, adjuvant, excipient, or vehicle with which the therapeutic is administered. In one embodiment, the therapeutically effective amount of the balanced PC composition of the present invention itself serves as the pharmaceutical carrier for the one or more cannabinoids (for example, and not by way of limitation, the balanced PC composition serves as a liposome, a micelle, or a small unilamellar vesicle (SUV) for the entrapment of the therapeutically effective amount of one or more cannabinoids. Such pharmaceutical carriers can be sterile liquids, such as water and oils, including those of petroleum, animal, vegetable or synthetic origin, such as peanut oil, soybean oil, mineral oil, sesame oil and the like. Preferred oil is essential fatty acids, linoleic acid and linolenic acid. Water is a preferred carrier when the pharmaceutical composition is administered intravenously. Saline solutions and aqueous dextrose and glycerol solutions can also be employed as liquid carriers, particularly for injectable solutions.

The terms "BodyBio balanced PC" and "balanced PC" are used interchangeably herein.

The active compositions of the invention having tissue modulatory activities as described herein are provided as isolated and substantially purified compounds in pharmaceutically acceptable formulations using formulation methods known to those of ordinary skill in the art. These formulations can be administered by standard routes.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In general, the combinations may be administered by the transdermal, intraperitoneal, intracranial, intracerebroventricular, intracerebral, intravaginal, intrauterine, oral, rectal, ophthalmic (including intravitreal or intracameral), nasal, topical (including buccal and sublingual), parenteral (including subcutaneous, intraperitoneal, intramuscular, intravenous, intradermal, intracranial, intratracheal, and epidural and nasal) administration. Parenteral administration includes direct or indirect injection into cells, tissues or organs in vivo, ex vivo or in vitro.

In one embodiment, the combination therapy comprising use of a first composition comprising a balanced PC composition and the second composition comprising one or more cannabinoids is administered through one or more different or the same routes of administration in a single or multiple regimen. In one embodiment, first composition comprising a balanced PC composition and the second composition comprising one or more cannabinoids can be administered by a variety of routes and modes of administration, including for example, and not by way of limitation, intravenous routes, transdermal routes, intranasal routes, parenteral routes, oral routes or a combination thereof. In one embodiment, the first composition comprising a balanced PC composition and the second composition comprising one or more cannabinoids is administered once, twice, three, four or more times daily through, IV routes, oral routes, or a combination of both.

Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachets indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided. The compositions are administered separately or are mixed together prior to administration.

In one embodiment, the first composition, the second composition or both may be incorporated into biodegradable polymers allowing for sustained release of the compound, the polymers being implanted in the vicinity of where drug delivery is desired or implanted so that the composition is slowly released systemically. Osmotic mini-pumps may also be used to provide controlled delivery of the first composition, the second composition or both through cannulae to the site of interest, such as directly into the site of injury. The biodegradable polymers and their use are described, for example, in detail in Brem et al., *J. Neurosurg.* 74: 441-446 (1991), which is hereby incorporated by reference in its entirety.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

The composition formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

In another embodiment, the composition of the invention comprises a therapeutically effective amount of a first composition comprising a balanced PC composition formulations and the second composition comprising one or more cannabinoids, in a suitable carrier.

A typical regimen for treatment of symptoms of diseases and disorders related to impaired development and activities of cells and tissues comprises administration of an effective amount of the composition as described above, administered as a single treatment, or repeated as enhancing or booster dosages, over a period up to and including one week to about 48 months or more.

Within other embodiments, the compositions may also be placed in any location such that the compounds or constituents are continuously released. The amount of the composition of the invention which will be effective in the treatment of symptoms of diseases and disorders related to impaired tissue development can be determined by standard clinical techniques. In addition, in vitro assays may optionally be employed to help identify optimal dosage ranges. In particular, the dosage of the compositions of the present invention will depend on the disease state of subject under treatment and other clinical factors such as weight and condition of the human or animal and the route of administration of the compounds or compositions. The precise dose to be employed in the formulation, therefore, should be decided according to the judgment of the health care practitioner and each patient's circumstances. Effective doses may be extrapolated from dose-response curves derived from in vitro or animal model test systems.

Various delivery systems are available and can be used to administer the compositions of the invention, i.e., encapsulation in liposomes, microparticles, microcapsules, recombinant cells capable of expressing the compound, receptor-mediated endocytosis. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (i.e., oral mucosa, rectal and intestinal mucosa, etc.) and may be administered together with other biologically active agents. Administration can be systemic or local.

In addition, it may be desirable to introduce the compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, i.e., by use of an inhaler or nebulizer, and formulation with an aerosolizing agent.

In a specific embodiment, it may be desirable to administer the compositions of the invention locally to the area in need of treatment; this may be achieved by, for example, and not by way of limitation, local infusion during surgery, topical application, i.e., in conjunction with a wound dressing after surgery, by injection, by means of a catheter, by means of a suppository, or by means of an implant, the implant being of a porous, non-porous, or gelatinous material, including membranes, such as sialastic membranes, or fibers. Preferably, when administering a protein such as cannabis, care must be taken to use materials to which the protein does not absorb or otherwise interact.

In one embodiment, the compound or composition can be delivered in a controlled release system. In one embodiment, a pump may be used. In another embodiment, polymeric materials can be used. In yet another embodiment, a controlled release system can be placed in proximity of the therapeutic target, i.e., the brain, thus requiring only a fraction of the systemic dose. Other controlled release systems are discussed in the review by Langer, Science 249:1527-1533 (1990).

Non-limiting representative examples of various dosage ranges for the first composition comprising a balanced PC composition and the second composition comprising one or more cannabinoids are as follows. In one embodiment, the first composition and/or the second composition is administered at a dosage of about 50 units/kg, 100 units/kg or 150 units/kg at a weekly or biweekly interval. In one embodiment, compositions disclosed herein comprise balanced PC and/or one or more cannabinoids in a total amount of between about 0.1% and about 95% by weight of the combination therapy composition, for example about 0.1%, about 0.2%, about 0.3%, about 0.4%, about 0.5%, about 0.6%, about 0.7%, about 0.8%, about 0.9%, about 1.0%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, or any numerical integer values there between.

The compositions of the invention can be in a form suitable for oral use, according to any technique suitable for the manufacture of oral pharmaceutical compositions as are within the skill in the art. For example, the phosphatidylcholine composition and the EFA composition can be formulated (either separately or together) into soft capsules, oily suspensions, or emulsions, optionally in admixture with pharmaceutically acceptable excipients.

The compositions of the invention are formulated into liquid, semi-liquid, suspension, or solid compositions, such as aqueous solutions, aqueous or oily suspensions, syrups or elixirs, emulsions, tablets, dispersible powders or granules, hard or soft capsules, optionally in admixture with pharmaceutically acceptable excipients.

5. Adjuvants, Carriers, and Diluents

As would be understood by one of ordinary skill in the art, when a composition of the present invention is provided to an individual, it can further comprise at least one of salts, buffers, adjuvants, or other substances which are desirable for improving the efficacy of the composition. Adjuvants are substances that can be used to specifically augment at least one immune response. Normally, the adjuvant and the composition are mixed prior to presentation to the immune system, or presented separately.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Adjuvants can be generally divided into several groups based upon their composition. These groups include lipid micelles, oil adjuvants, mineral salts (for example, AlK $(SO_4)_2$, AlNa $(SO_4)_2$, AlNH$_4$ $(SO_4)$), silica, kaolin, and certain natural substances, for example, wax D from Mycobacterium tuberculosis, substances found in *Corynebacterium parvum*, or *Bordetella pertussis*, Freund's adjuvant (DIFCO), alum adjuvant (Alhydrogel), MF-50 (Chiron) Novasomes™, or micelles, among others.

Suitable excipients for liquid formulation include water or saline, suspending agents such as sodium carboxymethyl-cellulose, methylcellulose, hydroxypropylmethyl-cellulose, sodium alginate, polyvinylpyrrolidone, gum tragacanth, and gum acacia; dispersing or wetting agents such as lecithin, condensation products of an alkylene oxide with fatty acids (e.g., polyoxethylene stearate), condensation products of ethylene oxide with long chain aliphatic alcohols (e.g., heptadecethyleneoxy-cetanol), condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyoxyethylene sorbitan monooleate).

Suitable excipients for solid formulations include calcium carbonate, sodium carbonate, lactose, calcium phosphate, or sodium phosphate; granulating and disintegrating agents such as maize starch, or alginic acid; binding agents such as starch, gelatin, or acacia; and lubricating agents such as magnesium stearate, stearic acids, or talc, and inert solid diluents such as calcium carbonate, calcium phosphate, or kaolin.

Other suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides.

The amount of the composition of the invention which will be effective in the treatment, inhibition and prevention of a disease or disorder associated with tissue or cell impairment can be determined by standard clinical techniques. In addition, in vitro assays may optionally be employed to help identify optimal dosage ranges.

In particular, the dosage of the composition of the present invention will depend on the disease state or condition being treated and other clinical factors such as weight and condition of the human or animal and the route of administration of the compound. The precise dose to be employed in the formulation, therefore, should be decided according to the judgment of the practitioner and each patient's circumstances. Effective doses may be extrapolated from dose-response curves derived from in vitro or animal model test systems.

For treating humans or animals, between approximately 0.5 to 500 mg/kilogram, is a typical broad range for administering the pharmaceutical composition of the invention. The methods of the present invention contemplate single as well as multiple administrations, given either simultaneously or over an extended period of time. It is to be understood that the present invention has application for both human and veterinary use.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

6. Test Kits

The invention also provides a combination therapy pack or kit comprising one or more containers filled with one or more compositions comprising a balanced PC composition and one or more cannabinoid compositions of the combined therapy of the invention. The kits are provided for the treatment of the symptoms of disease and disorders related to impaired development and activities of cells and tissues and in particular symptoms of disease related to imbalance of essential fatty acids, including seizure, depression, dementia, Alzheimer disease, and atherosclerosis. In one embodiment, the kit comprises instructions for treating seizures or a related disease or disorder as described supra in a subject and one or more of the following components: 1) a first composition comprising a balanced PC composition; 2) a second composition comprising one or more cannabinoids; and 3) optionally associated with such container(s) can be a notice in the form prescribed by a governmental agency regulating the manufacture, use or sale of pharmaceuticals or biological products, which notice reflects approval by the agency of manufacture, use or sale for human administration.

If a particular component is not included in the kit, the kit can optionally comprise information on where to obtain the missing component, for example an order form or uniform resource locator for the internet specifying a website where the component can be obtained. The instructions provided with the kit describe the practice of the methods of the invention as described above, and the route of administration and effective concentration and the dosing regimen for each of the compositions provided therein.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims. The contents of all references, patents and published patent applications cited throughout this application are expressly incorporated herein by reference.

EXAMPLES

Example 1

Production of BodyBio Balanced PC

BodyBio Balanced PC contains phosphatidyl-choline, phosphatidyl-ethanolamine, phosphatidyl-inositol, phosphatidic acid, and mixed glycerol phospholipids formulated as a water-soluble supplement extracted from soy lecithin (lecithin is oil based and is not water-soluble)(herein referred to as "BodyBio Balanced PC" or "balanced PC").

The fatty acids and phospholipid concentrations in the intermediate phosphatidylcholine compound are presented below. These percentage values provided below represent a non-limiting example of the fatty acid content and of the various phospholipids found in the composition.

Fatty Acid Content:
C16.0 16.1%
C16.1 0.1%
C18.0 4.1%
C18.1 10.0%
C18.2 55.30% (omega 6)
C18.3 14.0% (omega 3)
C22.0 0.4%
Phospholipids:
Phosphotidylcholine (PC): about 29%
Phosphotidylethanolamine (PE): about 16%
Phosphatidyl inositol (PI): about 9%
Phosphatidic Acid (PA): about 4%
Phosphatidylglycerol (PG): about 1%
Total PLs: about 61%

Example 2

Production of BodyBio Balanced PC Cannabinoid Combination Composition

Prepare BodyBio Balanced PC as in Example 1, Supra.
Prepare a 1:1 mix of Tetrahydrocannabinol (THC) and Cannabidiol (CBD).
Dissolve 1:1 mix of THC and CBD in pure deionized RO water.
Add ⅓ BodyBio balanced PC into the 1:1 mix of THC and CBD dissolved in pure deionized RO water and agitate violently for 5-10 seconds to produce a gelatinous state.

The BodyBio balanced PC composition—cannabinoid composition was then treated with a Sonic mixer (e.g., with a Branson 250 Sonic mixer) to generate a liposome size of approximately 5-10 microns.

In other embodiments, the liposomes are small unilamellar vesicles (SUVs) having sizes predominantly between 0.02 and 0.08 microns in size.

Example 3

Treatment of Patients with Epileptic Seizures with Combination Therapy

Case History: Intractable Epilepsy, Grand Mal Seizures
Patient Background: A 12-year old female presents with an intractable, inherited seizures disorder, Dravet Syndrome, and who is wheelchair bound. Seizure activity typically 3 grand mal seizures primarily while sleeping in the evening. Height: 4'6", Weight: 66 lbs.

Presenting symptoms include cognitive challenges, poor coordination, tremors, learning problems memory deficits, unable to walk, insomnia, heart palpitations, hair loss, urinary frequency, and drooling.

Clinical history: Dravet Syndrome severe myoclonic epilepsy of infancy, onset

Age 5 months

Ketogenic Diet (high fat) tried and failed. Break through, uncontrolled seizure activity with every anti-convulsant medication attempted.

Current Medications: none, failed every anti-seizure med, stopped at age 9.

Previous Meds: Anticonvulsants: Phenobarb, Valproic acid, Lamictal, Topamax, Ceptra, Tegretol Antibiotics, Antifungals.

Clinical Profile:
i) General Chemistry test results prior to oral and intravenous PC
  Electrolyte imbalance—low potassium −35%, low $CO_2$ −33%
  Hepatic stress—decrease in cholesterol −34%
  Poor nitrogen retention—low creatinine −135%
ii) Test results of red cell fatty acids
  Elevation of very long chain fatty acid depicting toxicity/suppressed peroxisomal function
  Demyelination with suppress of 16.0 DMA −98%, 18.0 DMA −49%, 18.1 DMA −39%
  Decreased Lipid content depicting poor membrane integrity −39%

Clinical Course:
Patient received oral and intravenous phospholipid therapy for 2 weeks. Patient exhibited a marked improvement in seizure activity, slowly decreasing to 1 seizure nightly in the first week of phospholipid therapy, and 1 seizure every other night in the second week. After cessation of the phospholipid therapy, there was an increase in seizure activity.

The use of liquid cannabinoids mixed with BodyBio balanced phosphatidylcholine (PC) in a combination therapy results in a sharp decrease in seizure activity approaching approximately 30% reduction in the incidence of seizures compared to use of BodyBio balanced phosphatidylcholine (PC) therapy alone.

Example 4

Treatment of Patients with Alzheimer's Disease with Combination Therapy

Case History: Alzheimer's disease
Patient Background: A 74-year old male presents with a diagnosis of Alzheimer's disease. Height: 5'10", Weight: 140 lbs.

Presenting Symptoms include poor short term memory, cognitive deficits (unable to read a clock, difficulty following directions, poor focus/attention, forgot the ability to use a computer, difficulty remembering where he placed objects, poor organization skills), anxiety, rage, word finding difficulty, aphasia, weight loss of 25# with reduced appetite, nocturia (up 2-3× each night), edema (ankles), pale skin, light sensitivity, blurred vision (no cataracts), vertigo at times, hoarseness, cold extremities (primarily hands, bilateral), muscle weakness in hands/arms, numbness in hands.

Dietary history: Self-imposed restriction of fat/oil and protein in the diet for the past 5 years for 'health' purposes
Family history of cancer, diabetes, cardiovascular disease
Current Medications: none
Clinical Profile:
i) General Chemistry test results prior to oral PC
  Electrolyte imbalance—low potassium −45%, low sodium −35%, low $CO_2$ −50%
  Hepatic stress—decrease in cholesterol −75%
  Hyperglycemia—increase in glucose +45%
  Poor nitrogen retention—low creatinine −65%, low albumin −45%
ii) Test results of red cell fatty acids
  Elevation of very long chain fatty acid depicting toxicity/suppressed peroxisomal function
  Overmyelination with increases of 16.0 DMA +311%, 18.0 DMA +125%, 18.1 DMA +226%
  Decreased Lipid content depicting poor membrane integrity −87%
  Deep suppression of Linoleic acid −73%
  Suppression of Arachidonic acid −58%

Clinical Course:
Patient received oral phospholipid therapy for 4 months. His diet was adjusted to increase protein and essential fatty acids were added as BodyBio Balance oil (linoleic acid) 2 Tablespoons twice daily and phosphatidylcholine liquid 1 Tablespoon twice daily. Patient experienced 60% improvement in cognitive function including his attention, memory, organizational skills, and communication. His anxiety diminished, his edema, pale skin tone, and numbness resolved. He gained muscle strength and his episodes and duration of rage improved by 30%.

The use of liquid cannabinoids BodyBio balanced phosphatidylcholine (PC) combination therapy results in a sharp decrease in rage associated behavior including rage episodes and rage duration. The BodyBio balanced phosphatidylcholine (PC) combination therapy further addresses his deficits in attention, memory, organizational skills, and communication and anxiety compared to use of BodyBio balanced phosphatidylcholine (PC) therapy alone.

Example 5

Treatment of Patients with Atherosclerosis with Combination Therapy

Case History Cardio 101
Patient Background: A 59-year old male presents with atherosclerosis, hyperlipidemia, hypertension, and hyperthyroidism.

Symptoms include fatigue, back pain. Patient had a history of kidney stones.

Family history of atherosclerosis, cancer, hypertension, alcoholism, neurological disease Current Medications: Thyroid, HCTZ/diuretic Clinical Profile:
  i) Test results before balanced PC cannabinoid combination therapy:
    Sharp increase in serum lipids with Triglycerides 581 (n=~100)
    Electrolyte imbalance—Potassium −33%
    Elevation in very long chain fatty acids
    Deficit in omega 6 gamma linolenic acid (GLA) −76% and dihomogamma linolenic acid (DGLA) −48%
    Deep suppression of red cell total lipid content −90%
    Gross increase in dimethyl acetals (DMAs) reflective of an increase in sphingomyelin.
    16:0 DMA +128% 18:0 DMA +51% 18:1 DMA +20%
  The dimethyl acetal status was determined by employing the red blood cell fatty acid test at The Peroxisomal Diseases Laboratory at the Kennedy Krieger Institute.
  ii) Test results after high dose [two tablespoons at ~45 grams per Tbls (corresponding to a final concentration of Balanced BodyBio PC of ~52% [composed of a complex of phospholipids, and of that complex ~½ is phosphatidylcholine] or ~12 grams of PC per Tbls.] oral balanced PC cannabinoid combination therapy:
    Stabilized Triglycerides 133 (n=~100)
    Electrolyte imbalance—Potassium −31%
    Elevation in very long chain fatty acids
    Continued deficit in omega 6 dihomogammal linolenic acid −60%
    Red cell total lipid content normalized
    Improvement in dimethyl acetal status reflective of sphingomyelin membrane content
    16:0 DMA +45% 18:0 DMA and 18:1 DMA Normalized (within +/−5% of the zero baseline)

Clinical Course: The DMAs are higher in patients with atherosclerosis and/or atherosclerotic plaques which is due to a heightened sphingomyelin to PC ratio. The use of the balanced PC alone to treat with atherosclerosis and/or atherosclerotic plaques results in a reduction of sphingomyelin (SM) at 45-50% of the membrane down to a ~20-25% concentration of SM value determined by measurement of the dimethyl acetyls (DMAs), with a corresponding return of the level of PC back towards its original normal 50% value. The use of Cannabis alone to treat the patient with atherosclerosis and/or atherosclerotic plaques results in no appreciable reduction of the sphingomyelin to PC ratio as determined by measurement of the dimethyl acetals (DMAs).

The patient with atherosclerosis and/or atherosclerotic plaques exhibits a marked improvement in his disturbed lipid biochemistry following the use of the balanced phosphatidylcholine cannabinoid combination therapy which is greater than the effect achieved with treatment with the balanced phosphatidylcholine alone. The patient also exhibits clinical improvement in cognition and energy which is greater than the effect of improvement in cognition and energy achieved with treatment with the balanced phosphatidylcholine alone.

The improvement in the patient's conditions is attributed to the BodyBio Inc balanced PC cannabinoid combination therapy which serves to reduce the sphingomyelin to PC ratio, and as a result, the DMAs are lowered by competitive inhibition.

The lowering of the DMA ratio results in a lowering of the plasminogens in the cell membrane which directly correlates with the lowered concentration of sphingomylenin and calcium in the cell membrane. This lowered concentration of sphingomyelin and calcium leads to a normalizing of the lipid bilayer membrane leaflets, a maximizing the integrity of the membrane, a lowering of the incidence of atherosclerosis and/or atherosclerotic plaques, and thus a more healthy heart, with the patient's sphingomyelin/PC ratios approaching a more normalized ratio of approximately ~20-25% to ~45-50% level respectively.

Case History Cardio 102

Patient Background: A 60-year old male presents with atherosclerosis, hyperlipidemia, and multiple sclerosis (relapsing remitting)

Symptoms include fatigue, back pain, insomnia and muscle weakness

Family history of atherosclerosis, neurological disease

Current Medications: None

Clinical Profile:
  i) Test results before balanced PC cannabinoid combination therapy:
    Increase in serum lipids with Triglycerides 155 (n=~100)
    Electrolyte imbalance—Sodium +30%, CO2 −25%, Calcium +43%
    Elevation in very long chain fatty acids
    Deficit in omega 6 gamma arachidonic acid −103%
    Deep suppression of red cell total lipid content −70%
    Gross increase in dimethyl acetals reflective of an increase in sphingomyelin
    16:0 DMA +180% 18:0 DMA +134% 18:1 DMA +166%
  The dimethyl acetal status was determined by employing the red blood cell fatty acid test as described supra.
  ii) Test results after high dose oral balanced PC cannabinoid combination therapy as described supra:
    Stabilized Triglycerides 116 (n=~100)
    Electrolyte imbalance—Sodium+30%, CO2 −25%, Calcium +43%
    Elevation in very long chain fatty acids
    Deficit in omega 6 arachidonic acid improved −59%
    Red cell total lipid content normalized
    Improvement in dimethyl acetal status reflective of sphingomyelin membrane content
    16:0 DMA, 18:0 DMA and 18:1 DMA all corrected (within +/−5% of the zero baseline).

Clinical Course: The DMAs are higher in atherosclerosis which is due to a heightened sphingomyelin to PC ratio. The patient has marked improvement in his disturbed lipid biochemistry following the use of the balanced phosphatidylcholine cannabinoid combination therapy. The patient also exhibits clinical improvement involved muscular and cardiac improvement. The improvement in his conditions is attributed to the BodyBio Inc balanced PC cannabinoid combination therapy which serves to reduce the sphingomyelin to PC ratio, and as a result, the DMAs are lowered.

The lowering of the DMA ratio results in a lowering of the plasminogens in the cell membrane which directly correlates with the lowered concentration of sphingomylenin and calcium in the cell membrane. This lowered concentration of sphingomylenin and calcium leads to a normalizing of the lipid bilayer membrane leaflets, a maximizing the integrity of the membrane, a lowering of the incidence of atherosclerosis and/or atherosclerotic plaques, and thus a more healthy heart, with the patient's sphingomyelin/PC ratios approaching a more normalized ratio of approximately 20%/50%, respectively.

Case History Cardio 103

Patient Background: A 76-year old male presents with an atherosclerosis, hyperlipidemia, bronchiectasis, atrial fibrillation, hypercoagulation, and post stroke.

Symptoms include fatigue, muscle weakness, shortness of breath, frequent urination, and sinusitis.

Family history of atherosclerosis and stroke.

Current Medications: Warfarin, antibiotics

Clinical Profile:

i) Test results before balanced PC cannabinoid combination therapy:

Sharp increase in serum lipids with LDL 181 (n=~100); Cholesterol 270

Electrolyte imbalance—increase in sodium +40

Sharp elevation in very long chain fatty acids, odd chain fatty acids

Gross deficit in omega 6 gamma linolenic acid −81%; dihomogamma linolenic acid −106%

Depression in red cell total lipid content −89%

Gross increase in dimethyl acetals reflective of an increase in sphingomyelin

16:0 DMA +136% 18:0 DMA +94% 18:1 DMA +101%

The dimethyl acetal status was determined by employing the red blood cell fatty acid test as described supra.

ii) Test results after high dose oral balanced PC cannabinoid combination therapy as described supra:

Slightly improved LDL 154 (n=~100); Cholesterol 243

Electrolyte imbalance—increase in sodium +50

Sharp elevation in very long chain fatty acids, odd chain fatty acids

Continued deficit in omega 6 gamma linolenic acid −81% and dihomogamma linolenic acid −102% due to poor compliance in taking oral lipid supplements Red cell total lipid content normalized Improvement in dimethyl acetal status reflective of sphingomyelin membrane content

16:0 DMA +67% 18:0 DMA +47% 18:1 DMA 53%

Clinical Course: The DMAs are higher in atherosclerosis which is due to a heightened sphingomyelin to PC ratio. Patient was resistant to taking his oral lipids but did receive intravenous phospholipid cannabinoid combination therapy. The Patient has marked improvement in the DMA/sphingomyelin status, stabilization of membrane phospholipids (normalization of red cell content) and serum lipids (triglycerides decreased) following the use of the balanced phosphatidylcholine cannabinoid combination therapy.

The Patient also exhibits clinical improvement in regard to fatigue, muscle strength, lung capacity and alertness. The improvement in his conditions is attributed to the BodyBio Inc balanced PC cannabinoid combination therapy which serves to reduce the sphingomyelin to PC ratio, and as a result, the DMAs are lowered.

The lowering of the DMA ratio results in a lowering of the plasminogens in the cell membrane which directly correlates with the lowered concentration of sphingomylenin and calcium in the cell membrane. This lowered concentration of sphingomyelin and calcium leads to a normalizing of the lipid bilayer membrane leaflets, a maximizing the integrity of the membrane, a lowering of the incidence of atherosclerosis and/or atherosclerotic plaques, and thus a more healthy heart, with the patient's sphingomyelin/PC ratios approaching a more normalized ratio of approximately 20%/50%, respectively.

Without intended to be limited to any particular mechanism of action, it is believed that the combination of BodyBio's balanced Phosphatidylcholine with one or more cannabinoids in the context of patients with atherosclerosis and/or atherosclerotic plaques may have i) interactions with one or more elements of the cell membrane; ii) direct actions on isolated arteries, causing both acute and time-dependent vasorelaxation, iii) protection against the vascular damage caused by a high glucose environment; and/or reduction of the vascular hyperpermeability associated with such cell membrane environments.

For example, and not by way of limitation, it has been shown by others that CB1 receptors are expressed in the human coronary atheromata, particularly in lesional macrophages, and that and that the endocannabinoid system was activated in patients with CAD. It has also been shown that CB1 receptor blockade significantly reduced the production of the proinflammatory mediators from human macrophages (Sugamura K, Sugiyama S, Nozaki T, et. al. 2009 January 6; 119(1):28-36). These results indicate the presence and activation of the endocannabinoid system in human atherosclerosis and suggest that CB1 receptor blockade modulates the inflammatory state in atheromata through its anti-inflammatory effects on macrophages.

The inclusion of one or more cannabinoids in combination with BodyBio's balanced Phosphatidylcholine may serve to function similarly to the endocannabinoids and synergystically bring about the blockade of one or more moieties in the cell membrane, including, for example, the CB1 receptor. The blockade of the CB1 receptor in turn modulates the inflammatory state in atheromata, which in turn in combination with BodyBio's balanced Phosphatidylcholine serves to reduce the sphingomyelin to PC ratio, and as a result, the DMAs are lowered by competitive inhibition.

The lowering of the DMA ratio results in a lowering of the plasminogens in the cell membrane which directly correlates with the lowered concentration of sphingomylenin and calcium in the cell membrane. This lowered concentration of sphingomylenin and calcium leads to a normalizing of the lipid bilayer membrane leaflets, a maximizing the integrity of the membrane, a lowering of the incidence of atherosclerosis and/or atherosclerotic plaques, and thus a more healthy heart, with the patient's sphingomyelin/PC ratios approaching more normalized ratios.

All references, including publications, patent applications, and patents, cited herein are hereby incorporated by reference to the same extent as if each reference were individually and specifically indicated to be incorporated by reference and were set forth in its entirety herein.

The use of the terms "a," "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

What is claimed is:

1. A composition for treating a subject having symptoms of diseases related to imbalance of essential fatty acids comprising: (a) a therapeutically effective amount of a first composition comprising a balanced phosphatidylcholine (PC); and (b) a therapeutically effective amount of a second composition comprising one or more cannabinoids, the balanced PC composition is a water-soluble supplement extracted from soy lecithin that comprises phospholipids and essential fatty acids; the phospholipids comprise phosphatidylcholine, phosphatidylethanolamine, and phosphatidylinositol; and the essential fatty acids comprise omega 6 and omega 3 fatty acids in a ratio of 4:1 respectively, and a pharmaceutically acceptable carrier or diluent, wherein said diseases comprise seizure, depression, Alzheimer's disease, and atherosclerosis.

2. The composition according to claim 1, wherein said treatment of diseases is manifested by a slowing of the progression of one or more symptoms comprising, visual loss or blurring, tingling, anxiousness, nausea, dizziness, numbness, confusion, uncontrollable muscle spasms, drooling or frothing at the mouth, falling, taste sensations, clenching teeth, sudden and rapid eye movements, grunting, incontinence, sudden mood changes, deafness, electric shock feeling, loss of consciousness, spacing out, panic, convulsion, difficulty talking, eyelid fluttering, eyes rolling up, foot stomping, hand waving, inability to move, lip smacking, making sounds, shaking, staring, stiffening, teeth clenching/grinding, tongue biting, tremors, twitching movements, breathing difficulty, heart racing, memory loss, writing difficulty, depression, sadness, exhaustion, headache, urge to urinate/defecate, plaques in coronary arteries, carotid arteries, or the peripheral arterial system, regression of atherosclerotic plaques in coronary arteries, carotid arteries, or the peripheral arterial system, or any combination thereof.

3. The composition according to claim 1, wherein the one or more cannabinoids comprise natural or synthetic variants of cannabinoids.

4. The composition according to claim 3, wherein the natural cannabinoids comprise those *Cannabis*-Derived Cannabinoids comprising Cannabinoids obtained from *Cannabis* indica plant comprising Cannabidiol (CBD), Cannabinol (CBN), Cannabigerol (CBG); Cannabichromene (CBC); Cannabicyclol (CBL); Cannabivarin (CBV); Tetrahydrocannabivarin (THCV); Cannabidivarin (CBDV); Cannabichromevarin (CBCV); Cannabigerovarin (CBGV); Cannabigerol Monomethyl Ether (CBGM); and Tetrahydrocannabinol (THC), or a combination thereof.

5. The composition of claim 4, wherein the natural cannabinoids further comprise phytocannabinoids derived from *Echinacea purpurea, Echinacea angustifolia, Echinacea pallida, Acmella oleracea, Helichrysum umbraculigerum*, and *Radula marginata*, or a combination thereof.

6. The composition of claim 3, wherein the synthetic cannabinoid variants comprise Dronabinol (Marinol) (Δ9-tetrahydrocannabinol (THC)), Nabilone (Cesamet), Sativex, and Rimonabant (SR141716), or a combination thereof.

7. The composition according to claim 1, wherein the balanced PC composition and the cannabinoids, are formulated in one or different solutions.

8. The composition according to claim 1, wherein the balanced PC composition and the cannabinoids are in a dry or a liquid formulation.

9. The composition according to claim 1, wherein the balanced PC composition and the cannabinoids are administered contemporaneously or at different time intervals.

10. A kit for treating or ameliorating one or more symptoms of seizures comprising:
   a) a first composition comprising a balanced phosphatidylcholine (PC) composition;
   b) a second composition comprising one or more cannabinoids; and
   c) instructions for the use of the first and second compositions and the constituents.

11. A method of achieving an enhanced therapeutic effectiveness of cannabinoids in a subject in need thereof comprising administrating one or more cannabinoids in combination with a balanced phosphatidylcholine composition, wherein the effective therapeutic concentration of the one or more cannabinoids is reduced by about 10-100 fold when administered with said balanced phosphatidylcholine as compared to a control group that had been administered said cannabinoids alone.

12. The method of claim 11, wherein reduced dosing of cannabinoids results in prevention or amelioration of one or more side effects or symptoms of use of cannabinoids comprising dysphoria, anxiety, panic, impairment of memory, reductions in psychomotor and cognitive performance, disordered perception of the passage of time, euphoria, schizophrenic psychosis, tiredness, dizziness, tachycardia, orthostatic hypotension, dry mouth, reduced lacrimation, muscle relaxation, increased appetite, potential irreversible cognitive impairments, or any combination thereof.

\* \* \* \* \*